US010829717B2

(12) United States Patent
Morikawa et al.

(10) Patent No.: US 10,829,717 B2
(45) Date of Patent: Nov. 10, 2020

(54) FINISHING AGENT COMPOSITION FOR TEXTILE PRODUCTS

(71) Applicant: Kao Corporation, Tokyo (JP)

(72) Inventors: Satoshi Morikawa, Wakayama (JP); Kana Tsumura, Wakayama (JP); Ayako Kusunoki, Wakayama (JP); Ayako Sakuraba, Wakayama (JP)

(73) Assignee: KAO CORPORATION, Tokyo (JP)

(*) Notice: Subject to any disclaimer, the term of this patent is extended or adjusted under 35 U.S.C. 154(b) by 75 days.

(21) Appl. No.: 16/341,761

(22) PCT Filed: Oct. 13, 2017

(86) PCT No.: PCT/JP2017/037170
§ 371 (c)(1),
(2) Date: Apr. 12, 2019

(87) PCT Pub. No.: WO2018/070516
PCT Pub. Date: Apr. 19, 2018

(65) Prior Publication Data
US 2020/0048582 A1  Feb. 13, 2020

(30) Foreign Application Priority Data

Oct. 14, 2016 (JP) ................. 2016-202595

(51) Int. Cl.
C11D 3/00 (2006.01)
C07C 309/20 (2006.01)
C11D 3/04 (2006.01)
C11D 3/06 (2006.01)
C11D 3/12 (2006.01)
C11D 3/34 (2006.01)
D06M 11/155 (2006.01)
D06M 13/256 (2006.01)

(52) U.S. Cl.
CPC ............ C11D 3/001 (2013.01); C07C 309/20 (2013.01); C11D 3/046 (2013.01); C11D 3/06 (2013.01); C11D 3/128 (2013.01); C11D 3/3463 (2013.01); D06M 11/155 (2013.01); D06M 13/256 (2013.01)

(58) Field of Classification Search
CPC ........... C11D 3/001; C11D 3/046; C11D 3/06; C11D 3/128; C11D 3/3463; C07C 309/20; D06M 11/155; D06M 13/256
See application file for complete search history.

(56) References Cited

U.S. PATENT DOCUMENTS

| 4,144,176 | A | 3/1979 | Kawanaka et al. | |
|---|---|---|---|---|
| 5,078,916 | A | 1/1992 | Kok et al. | |
| 6,331,511 | B1 | 12/2001 | Genova et al. | |
| 9,861,567 | B2 * | 1/2018 | Yoshikawa | ............ A61K 8/466 |
| 9,877,907 | B2 * | 1/2018 | Yoshikawa | ............ A61Q 5/02 |
| 10,184,076 | B2 * | 1/2019 | Barnes | ............ E21B 43/16 |
| 10,201,488 | B2 * | 2/2019 | Yoshikawa | ............ A61K 8/46 |
| 10,328,008 | B2 * | 6/2019 | Yoshikawa | ............ A61Q 5/04 |
| 2018/0353411 | A1 * | 12/2018 | Doi | ............ A61Q 5/02 |
| 2019/0390137 | A1 * | 12/2019 | Morikawa | ............ D06L 1/16 |
| 2020/0048582 | A1 * | 2/2020 | Morikawa | ............ C11D 11/0017 |
| 2020/0172833 | A1 * | 6/2020 | Morikawa | ............ C11D 3/0015 |
| 2020/0190432 | A1 * | 6/2020 | Morikawa | ............ C07C 309/20 |

FOREIGN PATENT DOCUMENTS

| CN | 105238573 A | | 1/2016 | |
|---|---|---|---|---|
| CN | 105273859 A | | 1/2016 | |
| CN | 105442324 A | | 3/2016 | |
| EP | 3467081 A1 | | 4/2019 | |
| GB | 2 236 538 A | | 4/1991 | |
| JP | S54-15091 A | | 2/1979 | |
| JP | S61-60796 A | | 3/1988 | |
| JP | H03-126793 A | | 5/1991 | |
| JP | 6-33398 B2 | | 5/1994 | |
| JP | 2000-038594 A | | 2/2000 | |
| JP | 2003081935 A | * | 3/2003 | |
| JP | 2014-076988 A | | 5/2014 | |
| WO | WO 2014/046175 A1 | | 3/2014 | |
| WO | WO-2017209117 A1 | * | 12/2017 | ............ C07C 43/11 |

OTHER PUBLICATIONS

International Preliminary Report on Patentability and English translation of the Written Opinion of the International Searching Authority for International Application No. PCT/JP2017/037170, dated Apr. 16, 2019.
Database WPI Week 201629, Thomson Scientific, London, GB; AN 2016-11097F, Jan. 27, 2016, XP002798708, 2 pages.
Database WPI Week 201642, Thomson Scientific, London, GB; AN 2016-20053N, Mar. 30, 2016, XP002798709, 1 page.
Extended European Search Report for European Application No. 17860498.9, dated Apr. 30, 2020.
International Search Report for PCT/JP2017/037170 (PCT/ISA/210) dated Nov. 28, 2017.
Stapersma et al., "Hydroxy Alkane Sulfonate (HAS), a New Surfactant Based on Olefins", Journal of the American Oil Chemists' Society, vol. 69, No. 1, Jan. 1992, p. 39-43.

* cited by examiner

Primary Examiner — Anthony J Green
(74) Attorney, Agent, or Firm — Birch, Stewart, Kolasch & Birch, LLP

(57) ABSTRACT

The present invention provides a fiber modifier composed of an internal olefin sulfonate having 17 or more and 24 or less carbons.

20 Claims, No Drawings

FINISHING AGENT COMPOSITION FOR TEXTILE PRODUCTS

FIELD OF THE INVENTION

The present invention relates to a fiber modifier, a finishing agent composition for textile products, a method for finishing textile products, a method for treating textile products, and use.

BACKGROUND OF THE INVENTION

Conventionally, anionic surfactants are known to be used as softeners. JP-A 54-15091 discloses a textile treatment agent that contains a salt of α-olefin sulfonic acid having 20 or more carbons, particularly, 20 or more and 30 or less carbons and imparts smoothness and softness to textile products.

Meanwhile, JP-A 2014-76988 discloses an internal olefin sulfonate composition containing (A) an internal olefin sulfonate having 16 carbons and/or (B) an internal olefin sulfonate having 18 carbons, wherein a content mass ratio (A/B) of component (A) to component (B) is 0/100 to 70/30, and is excellent in foaming properties, foam quality, quick foamability, foam breakability, particularly foam quality, particularly during hair washing.

SUMMARY OF THE INVENTION

In a process of washing textile products, including softening, the textile products are generally washed, rinsed, and softened. Conventionally, detergents mainly containing anionic surfactants have been mostly used for washing, and softeners containing cationic surfactants have been mostly used for softening. However, a short rinse time or a small amount of water used for rinsing may result in insufficient rinsing, so that the anionic surfactants used for washing are carried into the treatment bath for softening, thereby counteracting the effects of cationic surfactants, in some cases. Further, detergents mainly containing nonionic surfactants are also known, but insufficient rinsing may cause hard texture of textile products in some cases, even if softening is performed. Further, use of softeners mainly containing cationic surfactants may possibly cause a decrease in water absorbency of textile products softened as compared with the original water absorbency of the textile products.

The α-olefin sulfonate having 20 to 30 carbons according to JP-A 54-15091 can finish the textile products with softness, but the effects thereof are desired to be further improved.

The present invention relates to a fiber modifier which finishes textile products with a soft texture without reducing the original water absorbency of the textile products. The present invention also relates to a finishing agent composition for textile products, containing the fiber modifier. In particular, the present invention relates to a softening agent composition for textile products, imparting excellent softness to the textile products.

The inventors have found that an internal olefin sulfonate having a specific carbon chain length can finish fibers with a soft texture without reducing the water absorbency of fibers. The inventors have found that an internal olefin sulfonate having a specific carbon chain length can impart a soft texture to fibers.

The present invention relates to a fiber modifier composed of an internal olefin sulfonate having 17 or more and 24 or less carbons. Further, the present invention relates to a finishing agent composition for textile products, containing an internal olefin sulfonate having 17 or more and 24 or less carbons. Further, the present invention relates to a softening agent composition for textile products, containing an internal olefin sulfonate having 17 or more and 24 or less carbons.

Further, the present invention relates to a method for finishing textile products, the method including contacting the textile products with a treatment liquid for textile products containing water and an internal olefin sulfonate having 17 or more and 24 or less carbons in an amount of 0.002% by mass or more and 6% by mass or less relative to the textile products. Further, the present invention relates to a method for softening textile products, the method including contacting the textile products with a treatment liquid for textile products containing water and an internal olefin sulfonate having 17 or more and 24 or less carbons in an amount of 0.002% by mass or more and 6% by mass or less relative to the textile products.

Further, the present invention relates to a method for treating textile products, the method including: step 1 of washing the textile products with a washing liquid containing one or more surfactants selected from anionic surfactants and nonionic surfactants; and step 2 of contacting the textile products after step 1 with a treatment liquid for textile products containing water and an internal olefin sulfonate having 17 or more and 24 or less carbons in an amount of 0.002% by mass or more and 6% by mass or less relative to the textile products.

Further, the present invention relates to use of an internal olefin sulfonate having 17 or more and 24 or less carbons as a fiber modifier. Further, the present invention relates to use of an internal olefin sulfonate having 17 or more and 24 or less carbons as a finishing agent for textile products. Further, the present invention relates to use of an internal olefin sulfonate having 17 or more and 24 or less carbons as a softening agent for textile products.

The fiber modifier, the finishing agent composition for textile products, the method for finishing textile products, and the method for treating textile products according to the present invention can finish textile products with a soft texture without reducing the original water absorbency of the textile products. For example, in the case of using the present invention in the field of softening textile products, the softening agent composition for textile products, the method for softening textile products, and the method for treating textile products according to the present invention can impart a soft texture to the textile products.

EMBODIMENTS OF THE INVENTION

<Internal Olefin Sulfonate Having 17 or More and 24 or Less Carbons>

An internal olefin sulfonate having 17 or more and 24 or less carbons [which may be hereinafter referred to as component (A)] has the effect of finishing textile products with softness without reducing the original water absorbency of the textile products. The number of carbons of the internal olefin sulfonate having 17 or more and 24 or less carbons indicates the number of carbons of an internal olefin to which sulfonates are covalently bound. The internal olefin sulfonate having 17 or more and 24 or less carbons has 17 or more, preferably 18 or more carbons, so as to be capable of softening textile products, and has 24 or less, preferably 22 or less, more preferably 20 or less, further preferably 19 or less carbons, so as to be capable of maintaining the effect of finishing the textile products with softness even if the temperature of the treatment liquid for textile products containing component (A) is low.

The internal olefin sulfonate having 17 or more and 24 or less carbons has 17 or more, preferably 18 or more carbons, so as to be capable of finishing textile products with a soft texture, and has 24 or less, preferably 22 or less, more preferably 20 or less, further preferably 19 or less carbons, so as to be capable of maintaining the original water absorbency of the textile products. The number of carbons falling within such a range allows the textile products to be finished with a soft texture and the original water absorbency of the textile products to be maintained.

The internal olefin sulfonate having 17 or more and 24 or less carbons contains an internal olefin sulfonic acid having 18 or more carbons in an amount of preferably 80% by mass or more, further preferably 90% by mass or more, so as to be capable of finishing textile products with a soft texture, and contains an internal olefin sulfonate having 20 or more and 24 or less carbons in an amount of preferably 20% by mass or less, further preferably 10% by mass or less, more preferably 5% by mass or less, furthermore preferably 3% by mass or less, furthermore preferably 1% by mass or less, furthermore preferably 0% by mass, so as to be capable of maintaining the original water absorbency of the textile products.

The internal olefin sulfonate of the present invention is a sulfonate obtained by sulfonation, neutralization, and hydrolysis of an internal olefin (an olefin having a double bond inside the olefin chain) having 17 or more and 24 or less carbons as a raw material.

Such an internal olefin includes the case of containing a slight amount of so-called alpha olefin (which will be hereinafter referred to also as α-olefin) in which the double bond is located at the 1-position of the carbon chain.

Further, the sulfonation of the internal olefin quantitatively produces β-sultone, the β-sultone partially transforms into γ-sultone and olefin sulfonic acid, and these further convert into hydroxyalkanesulfonate and olefin sulfonate in the neutralization and hydrolysis steps (for example, J. Am. Oil Chem. Soc. 69, 39 (1992)). Here, the hydroxy group of the hydroxyalkanesulfonate obtained is present inside the alkane chain, and the double bond of the olefin sulfonate is present inside the olefin chain. Further, the products to be obtained are mainly mixtures of these and may partially contain a slight amount of hydroxyalkanesulfonate having a hydroxy group at the end of the carbon chain or olefin sulfonate having a double bond at the end of the carbon chain in some cases.

In the present description, these products and mixtures thereof will be collectively referred to as internal olefin sulfonate (component (A)). Further, the hydroxyalkanesulfonate will be referred to as the hydroxy form of the internal olefin sulfonate (which will be hereinafter referred to also as HAS), and the olefin sulfonate will be referred to as the olefin form of the internal olefin sulfonate (which will be hereinafter referred to also as IOS).

The mass ratio of HAS and IOS of the compounds in component (A) can be determined by high performance liquid chromatography mass spectrometer (which will be hereinafter abbreviated as HPLC-MS). Specifically, the mass ratio can be determined from the HPLC-MS peak area of component (A).

Examples of the salt of the internal olefin sulfonate include alkali metal salts, alkaline earth metal (½ atom) salts, ammonium salts, or organic ammonium salts. Examples of the alkali metal salts include Na salts and K salts. Examples of the organic ammonium salts include alkanol ammonium salts having 2 or more and 6 or less carbons. Examples of the alkanol ammonium salts having 2 or more and 6 or less carbons include monoethanol ammonium salt, diethanol ammonium salt, triethanol ammonium salt, N-methyl ethanol ammonium salt, N-methyl diethanol ammonium salt, and N-methyl triethanol ammonium salt.

In the case of using the mass of component (A) in the present invention, a value obtained by calculating the counter ions of component (A) in terms of sodium salts is used.

As is obvious from the aforementioned fabrication method, the internal olefin sulfonate of component (A) has a sulfonate group present inside the carbon chain of the internal olefin sulfonate, that is, inside the olefin chain or the alkane chain, and may partially contain a slight amount of a sulfonate group present at the end of the carbon chain.

In the present invention, the content of the internal olefin sulfonate with the sulfonate group at position 2 in component (A) is preferably 10% by mass or more, more preferably 15% by mass or more, more preferably 20% by mass or more, more preferably 25% by mass or more, more preferably 30% by mass or more, more preferably 35% by mass or more, more preferably 40% by mass or more, and preferably 60% by mass or less, in component (A), so as to be capable of finishing the textile products with more softness.

The content of the internal olefin sulfonate with the sulfonate group at position 6 or higher and 9 or lower in component (A) is preferably 50% by mass or less, more preferably 45% by mass or less, further preferably 40% by mass or less, so as to be capable of finishing the textile products with more softness and is preferably 5% by mass or more, more preferably 7% by mass or more, further preferably 9% by mass or more, furthermore preferably 10% by mass or more, so as to be capable of maintaining the effect of finishing the textile products with softness even if the temperature of the treatment liquid for textile products containing component (A) is low.

Component (A) can contain 1-olefin sulfonate in an amount of up to 10% by mass in component (A), so as to be capable of finishing the textile products with more softness even if the temperature of the treatment liquid containing component (A) and water that is used for finishing, particularly, softening the textile products is as low as 0° C. or more and 15° C. or less. The content of 1-olefin sulfonate in component (A) is preferably 10% by mass or less, more preferably 7% by mass or less, further preferably 5% by mass or less, more preferably 3% by mass or less. Further, the content is preferably 0.01% by mass or more for reducing the production cost and improving the productivity.

Here, the 1-olefin sulfonate is an olefin sulfonate with the sulfonate group at position 1 of the olefin chain or the alkane chain. The position of the sulfonate group in such a compound is a position when the carbon at the end of the olefin chain or the alkane chain is regarded as position 1.

Component (A) of the present invention preferably contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less, so as to be capable of finishing textile products with a soft texture and maintaining the original water absorbency of the textile products. That is, component (A) of the present invention is preferably an internal olefin sulfonate having 17 or more and 24 or less carbons, wherein the mass ratio (IO-1S)/(IO-2S) of an internal olefin sulfonate having 17 or more and 24 or less carbons with the sulfonate group at position 2 or higher and 4 or lower (IO-1S) to an internal olefin sulfonate having 17 or more and 24 or less carbons with the sulfonate group at position 5 or higher (IO-2S) is 0.6 or more and 6 or less, so as to be capable of finishing textile products with a soft texture and maintaining the original water absorbency of the textile products.

The mass ratio (IO-1S)/(IO-2S) of the content of (IO-1S) to the content of (IO-2S) in component (A) is preferably 0.6 or more, more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, so as to be capable of finishing textile products with softness, and is preferably 6 or less, more preferably 5.5 or less, further preferably 5.0 or less, furthermore preferably 4.5 or less, so as to be capable of maintaining the original water absorbency of the textile products.

The content of each compound with a different position of the sulfonate group in component (A) can be determined by high performance liquid chromatography/mass spectrometer (which will be hereinafter abbreviated as HPLC-MS). The content of each compound with a different position of the sulfonate group in the present description is determined as a mass ratio based on the HPLC-MS peak area of the compound with the sulfonate group located at each position in all HAS of component (A).

Here, the HAS is the hydroxy form of internal olefin sulfonate, that is, hydroxyalkanesulfonate among the compounds produced by the sulfonation of the internal olefin sulfonic acid.

In the present invention, the internal olefin sulfonate having 17 or more and 24 or less carbons with the sulfonate group at position 2 or higher and 4 or lower (IO-1S) means a sulfonate with the sulfonate group at position 2 or higher and 4 or lower in the HAS having 17 or more and 24 or less carbons.

Further, the internal olefin sulfonate having 17 or more and 24 or less carbons with the sulfonate group at position 5 or higher (IO-2S) means a sulfonate with the sulfonate group at position 5 or higher in the HAS having 17 or more and 24 or less carbons.

The internal olefin sulfonate that is component (A) contains the internal olefin sulfonate having 17 or more and 24 or less carbons with the sulfonate group at position 2 or higher and 4 or lower (IO-1S) and the internal olefin sulfonate having 17 or more and 24 or less carbons with the sulfonate group at position 5 or higher (IO-2S). The maximum value of the position of bonding of the sulfonate group in the internal olefin sulfonate (IO-2S) varies depending on the number of carbons.

The mass ratio (IO-1S)/(IO-2S) in component (A) is based on component (A) that is finally obtained. For example, even an internal olefin sulfonate obtained by mixing internal olefin sulfonates with a mass ratio (IO-1S)/(IO-2S) that is out of the aforementioned ranges is also regarded as the internal olefin sulfonate that is component (A), as long as the mass ratio (IO-1S)/(IO-2S) in the composition of the internal olefin sulfonate falls within the aforementioned ranges.

The internal olefin sulfonates can be a mixture of a hydroxy form and an olefin form. In component (A), the mass ratio (hydroxy form/olefin form) of the content of the hydroxy form in the internal olefin sulfonate to the content of the olefin form in the internal olefin sulfonate can be 50/50 or more and 100/0 or less, 60/40 or more and 100/0 or less, 70/30 or more and 100/0 or less, 75/25 or more and 100/0 or less, or 75/25 or more and 95/5 or less.

In component (A), the mass ratio of the content of the hydroxy form in the internal olefin sulfonate to the content of the olefin form in the internal olefin sulfonate can be determined by the method described in Examples, after the hydroxy form and the olefin form are separated by HPLC from component (A) or the surfactant composition obtained.

Component (A) can be produced by sulfonation, neutralization, and hydrolysis of an internal olefin having 17 or more and 24 or less carbons that is a raw material.

The sulfonation can be carried out, for example, by reacting 1.0 to 1.2 mol of sulfur trioxide gas with 1 mol of the internal olefin. The reaction temperature can be 20 to 40° C.

The neutralization is carried out, for example, by reacting an alkali aqueous solution such as sodium hydroxide, ammonia, and 2-aminoethanol in an amount of 1.0 to 1.5 molar times the theoretical value of the sulfonate group.

The hydrolysis may be carried out, for example, by reaction at 90 to 200° C. for 30 minutes to 3 hours in the presence of water.

These reactions can be continuously carried out. After the completion of the reactions, purification can be carried out by extraction, washing, or the like.

When producing the internal olefin sulfonate (A), the treatment such as sulfonation, neutralization, and hydrolysis may be performed using a raw material internal olefin having a carbon number distribution within the range of 17 or more and 24 or less. Alternatively, the treatment such as sulfonation, neutralization, and hydrolysis may be performed using a raw material internal olefin having a single carbon atom. Alternatively, a plurality of types of internal olefin sulfonates having different numbers of carbons that have been produced in advance as required may be mixed.

In the present invention, the internal olefin is an olefin having a double bond inside the olefin chain, as described above. The internal olefin that is component (A) has 17 or more and 24 or less carbons. One type of internal olefin alone may be used for component (A), or two or more types may be used in combination.

In the case of obtaining the internal olefin sulfonate that is component (A) by sulfonation, neutralization, and hydrolysis of the raw material internal olefin, the total content of internal olefins with double bonds at position 2 in the raw material internal olefin is preferably 10% by mass or more, more preferably 15% by mass or more, more preferably 20% by mass or more, more preferably 25% by mass or more, more preferably 30% by mass or more, more preferably 35% by mass or more, more preferably 40% by mass or more, and preferably 60% by mass or less, in component (A), for improving the softness of the textile products.

The total content of olefins with double bonds at position 1, so-called alpha olefins, in the raw material internal olefin is preferably 10% by mass or less, more preferably 7% by mass or less, further preferably 5% by mass or less, more preferably 3% by mass or less, so as to be capable of finishing the textile products with more softness, even if the temperature of water used for washing is as low as 0° C. or more and 15° C. or less. For reducing the production cost and improving the productivity, the total content is preferably 0.01% by mass or more.

The content of olefins with double bonds at position 6 or higher and 9 or lower in the raw material internal olefin is preferably 50% by mass or less, more preferably 45% by mass or less, more preferably 40% by mass or less, more preferably 35% by mass or less, more preferably 30% by mass or less, more preferably 25% by mass or less, more preferably 20% by mass or less, more preferably 15% by mass or less, more preferably 10% by mass or less, so as to be capable of finishing the textile products with more softness.

The distribution of double bonds in the raw material internal olefin can be determined, for example, by gas chromatography and mass spectrometry (which will be hereinafter abbreviated as GC-MS). Specifically, the positions of double bonds can be identified by accurately separating each component having a different carbon chain length and a different position of the double bond using a gas chromatograph analyzer (which will be hereinafter abbreviated as GC), and then applying the component to a mass spectrometer (which will be hereinafter abbreviated as MS), so that the proportion of the component can be determined from the GC peak area.

(1) Determination Conditions
(i) Method for Determining Double Bond Positions in Raw Material Internal Olefin The double bond positions in the internal olefin were determined by gas chromatography (which will be hereinafter abbreviated as GC). Specifically, after a dithiolated derivative was obtained by reacting dimethyl disulfide with the internal olefin, each component was separated by GC. As a result, the double bond positions in the internal olefin were determined from each peak area.

The devices and analysis conditions used for the determination were as follows.
GC apparatus: "HP6890" (manufactured by Hewlett-Packard Company)
Column: "Ultra-Alloy-1HT Capillary column" (30 m×250 μm×0.15 μm, manufactured by Frontier Laboratories Ltd.)
Detector: (hydrogen flame ion detector (FID)),
Injection temperature: 300° C.
Detector temperature: 350° C.
He flow rate: 4.6 mL/minute (ii) Method for Determining Mass Ratio of Hydroxy Form to Olefin Form The mass ratio, hydroxy form/olefin form, was determined by HPLC-MS. Specifically, the hydroxy form and the olefin form were separated from each other by HPLC and were each applied to MS for identification. As a result, the proportion of each form was determined from the HPLC-MS peak area.

The devices and the conditions used for the determination were as follows. HPLC apparatus: "Agilent Technology 1100" (manufactured by Agilent Technologies, Inc.)
Column: "L-columnODS" (4.6×150 mm, manufactured by Chemicals Evaluation and Research Institute, Japan)
Sample preparation: Diluted 1000-fold with methanol
Eluent A: 10 mM ammonium acetate-added water
Eluent B: 10 mM ammonium acetate-added methanol
Gradient: 0 minutes (A/B=30/70%)→10 minutes (30/70%)→55 minutes (0/100%)→65 minutes (0/100%)→66 minutes (30/70%)→75 minutes (30/70%) MS apparatus "Agilent Technology 1100 MSSL (C1946D)" (manufactured by Agilent Technologies, Inc.)
MS detection: Anion detection, m/z: 60 to 1600, UV: 240 nm <Fiber Modifier, Finishing Agent Composition for Textile Products, Particularly, Softening Agent Composition for Textile Products>

The present invention discloses a fiber modifier composed of an internal olefin sulfonate having 17 or more and 24 or less carbons and a finishing agent composition for textile products containing the modifier. The finishing agent composition for textile products according to the present invention is a finishing agent composition for textile products, containing the internal olefin sulfonate having 17 or more and 24 or less carbons.

Examples of the finishing agent composition for textile products according to the present invention include a softening agent composition for textile products, containing the fiber modifier composed of the internal olefin sulfonate having 17 or more and 24 or less carbons. The softening agent composition for textile products according to the present invention is a softening agent composition for textile products, containing the internal olefin sulfonate having 17 or more and 24 or less carbons.

Further, the present invention discloses use of an internal olefin sulfonate having 17 or more and 24 or less carbons as a finishing agent composition for textile products, particularly, as a softening agent for textile products.

The content of component (A) in the finishing agent composition for textile products, particularly, the softening agent composition for textile products according to the present invention is preferably 1% by mass or more, more preferably 2% by mass or more, further preferably 3% by mass or more, furthermore preferably 4% by mass or more, furthermore preferably 5% by mass or more, for further improving the effect of imparting softness to the textile products per mass of the finishing agent composition for textile products, particularly, the softening agent composition for textile products when washing the textile products. Further, the content of component (A) in the finishing agent composition for textile products, particularly, the softening agent composition for textile products according to the present invention is preferably 95% by mass or less, more preferably 90% by mass or less, further preferably 80% by mass or less, furthermore preferably 70% by mass or less, furthermore preferably 60% by mass or less, furthermore preferably 50% by mass or less, furthermore preferably 40% by mass or less, so as to be capable of finishing the textile products with more softness even if the contact time between water containing component (A) and the textile products is short.

A value obtained by calculating counter ions as sodium ions is used as the mass of component (A) contained in the finishing agent composition for textile products, particularly, the softening agent composition for textile products.

In the finishing agent composition for textile products, particularly, the softening agent composition for textile products according to the present invention, the content of an internal olefin sulfonate having 16 or less carbons is preferably 90 parts by mass or less, more preferably 80 parts by mass or less, further preferably 70 parts by mass or less, furthermore preferably 60 parts by mass or less, furthermore preferably 50 parts by mass or less, furthermore preferably 40 parts by mass or less, furthermore preferably 30 parts by mass or less, furthermore preferably 20 parts by mass or less, furthermore preferably 10 parts by mass or less, relative to a content of component (A) of 100 parts by mass. In the finishing agent composition for textile products, particularly, the softening agent composition for textile products according to the present invention, the content of the internal olefin sulfonate having 16 or less carbons is preferably 0 parts by mass relative to a content of component (A) of 100 parts by mass, that is, the internal olefin sulfonate having 16 or less carbons is preferably not contained.

<Fibers>

Fibers constituting the textile products to be treated with the finishing agent composition for textile products, particularly, the softening agent composition for textile products according to the present invention may be any one of hydrophobic fibers and hydrophilic fibers. Examples of the hydrophobic fibers include protein fibers (such as milk protein casein fibers and Promix), polyamide fibers (such as nylon), polyester fibers (such as polyester), polyacrylonitrile fibers (such as acrylic), polyvinyl alcohol fibers (such as vinylon), polyvinyl chloride fibers (such as polyvinyl chloride), polyvinylidene chloride fibers (such as vinylidene), polyolefin fibers (such as polyethylene and polypropylene), polyurethane fibers (such as polyurethane), polyvinyl chloride/polyvinyl alcohol copolymer fibers (such as polychlal), polyalkylene paraoxybenzoate fibers (such as benzoate), and polyfluoroethylene fibers (such as polytetrafluoroethylene). Examples of the hydrophilic fibers include seed hair fibers (such as cotton and kapok), bast fibers (such as hemp, flax, ramie, cannabis, and jute), leaf fibers (such as abaca and sisal), palm fibers, rush, straw, animal hair fibers (such as wool, mohair, cashmere, camel hair, alpaca, vicuna, and angola), silk fibers (such as domestic silkworm silk and wild silkworm silk), feathers, and cellulose fibers (such as rayon, polynosic, cupra, and acetate).

The fibers are preferably fibers containing cotton fibers, in that the softness of the fibers after the treatment with the finishing agent composition for textile products, particularly, the softening agent composition for textile products according to the present invention is more easily felt. For further improving the softness of the fibers, the content of the cotton fibers in the fibers is preferably 5% by mass or more, preferably 10% by mass or more, preferably 15% by mass or more, preferably 20% by mass or more, and the upper limit is 100% by mass.

<Textile Products>

In the present invention, the textile products mean cloths such as woven fabrics, knittings, and non-woven fabrics using hydrophobic fibers or hydrophilic fibers mentioned above, and textile products obtained by using the cloths, such as undershirts, T-shirts, business shirts, blouses, slacks, hats, handkerchiefs, towels, sheets, pillowcases, knits, socks, underwears, and tights. The textile products are preferably textile products containing cotton fibers, in that the softness of the fibers after the treatment with the finishing agent composition for textile products, particularly, the softening agent composition for textile products according to the present invention is more easily felt. For further improving the softness of the fibers, the content of the cotton fibers in the textile products is preferably 5% by mass or more, preferably 10% by mass or more, preferably 15% by mass or more, preferably 20% by mass or more, and the upper limit is 100% by mass.

<Optional Components>

The finishing agent composition for textile products, particularly, the softening agent composition for textile products according to the present invention can contain components selected from components (B) to (E) below. The finishing agent composition for textile products, particularly, the softening agent composition for textile products according to the present invention preferably contains component (B). In the finishing agent composition for textile products, particularly, the softening agent composition for textile products according to the present invention, the content of component (C) preferably falls within a predetermined range. The finishing agent composition for textile products, particularly, the softening agent composition for textile products according to the present invention preferably contains component (D).

<Component (B)>

For further enhancing the effect of finishing the textile products with softness, the finishing agent composition for textile products, particularly, the softening agent composition for textile products according to the present invention can contain a polyvalent metal salt as component (B).

Examples of the polyvalent metal salt that is component (B) include one or more polyvalent metal salts selected from inorganic polyvalent metal salts and organic polyvalent metal salts.

Preferable examples of the polyvalent metal salts include one or more polyvalent metal salts selected from inorganic divalent metal salts, inorganic trivalent metal salts, organic divalent metal salts, and organic trivalent metal salts.

Examples of the inorganic divalent metal salts include calcium salts and magnesium salts.

Examples of the inorganic trivalent metal salts include aluminum salts.

For further enhancing the effect of finishing the textile products with softness, the inorganic polyvalent metal salts are preferably inorganic divalent metal salts, preferably one or more metal salts selected from calcium salts and magnesium salts.

Examples of the salts of the polyvalent metal salts include one or more salts selected from halogen salts, sulfates, nitrates, alkyl sulfates having 1 or more and 3 or less carbons, and carboxylates having 1 or more and 6 or less carbons. Examples of the halogens of the halogen salts include chlorine, bromine, and iodine. As the alkyl sulfates having 1 or more and 3 or less carbons, methyl sulfate and ethyl sulfate are preferable. Examples of the carboxylates having 1 or more and 6 or less carbons include acetate, glycolate, propionate, maleate, fumarate, and citrate.

The inorganic polyvalent metal salts are preferably one or more inorganic polyvalent metal salts selected from calcium chloride, magnesium chloride, aluminum chloride, magnesium sulfate, and aluminum sulfate, more preferably one or more inorganic polyvalent metal salts selected from calcium chloride, magnesium chloride, and magnesium sulfate.

The organic polyvalent metal salts are preferably organic polyvalent metal salts having 1 or more and 8 or less carbons, more preferably one or more organic polyvalent metal salts selected from sulfonic acid polyvalent metal salts having 1 or more and 8 or less carbons, sulfate ester polyvalent metal salts having 1 or more and 8 or less carbons, and carboxylic acid polyvalent metal salts having 1 or more and 8 or less carbons, further preferably one or more organic polyvalent metal salts selected from magnesium methylsulfate, magnesium ethylsulfate, magnesium glycolate, and magnesium citrate.

Component (B) is preferably an inorganic polyvalent metal salt, more preferably one or more polyvalent metal salts selected from inorganic divalent metal salts and inorganic trivalent metal salts, further preferably one or more polyvalent metal salts selected from inorganic divalent metal salts, furthermore preferably one or more polyvalent metal salts selected from inorganic calcium salts and inorganic magnesium salts.

When the finishing agent composition for textile products, particularly, the softening agent composition for textile products according to the present invention contains component (B), the content of component (B) is preferably 10 mg/kg or more, more preferably 20 mg/kg or more, further preferably 30 mg/kg or more, and preferably 20% by mass or less, more preferably 15% by mass or less, further preferably 10% by mass or less, in that the effect of finishing the textile products with softness can be more enhanced.

<Component (C)>

The finishing agent composition for textile products, particularly, the softening agent composition for textile products according to the present invention can contain a metal ion chelating agent as component (C) without inhibiting the effects of the present invention. Component (C) may be not blended into the composition, since the finishing agent composition for textile products, particularly, the softening agent composition for textile products according to the present invention is preferably subjected to softening using water containing hardness components.

Water containing hardness components is preferably used as the water used in washing or finishing the textile products, for imparting a better finish effect to the textile products, but if the textile products are repeatedly washed or finished with water having a high content of hardness components, the hardness components accumulate in the textile products, and the textile products may be finished with hardness. The finishing agent composition for textile products according to the present invention containing component (C), particularly, the softening agent composition for textile products according to the present invention containing an appropriate amount of component (C) can suppress a reduction in softness, even if the textile products are repeatedly washed or finished with water having a high content of hardness components.

Component (C) is preferably a metal ion chelating agent capable of chelating divalent or higher valent metal ions.

Examples of component (C) of the present invention include one or more metal ion chelating agents selected from (C1) metal ion chelating agents that are inorganic compounds and (C2) metal ion chelating agents that are organic compounds. Component (C) is preferably one or more metal ion chelating agents selected from (C1) metal ion chelating agents that are inorganic compounds.

[(C1) Metal Ion Chelating Agents that are Inorganic Compounds]

Examples of (C1) metal ion chelating agents that are inorganic compounds include one or more metal ion chelating agents selected from (C1-1) alkali metal silicates, (C1-2) aluminosilicates, and (C1-3) tripolyphosphates. Hereinafter, these components will be described.

(C1-1) alkali metal silicates are alkali metal salts of silicic acid ($SiO_2$), and compounds with $SiO_2/M_2O$ (where M represents an alkali metal) in alkali metal silicates of 0.5 to 2.6 are generally used. More specifically, they have a composition represented by formula (I) below:

$$x(M_2O).y(SiO_2).z(Me_mO_n).w(H_2O) \tag{I}$$

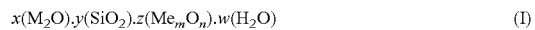

where M represents one or a combination of two or more selected from the group consisting of alkali metals, Me represents one or two or more elements selected from group II, group III, group IV, and group VIII in the periodic table of elements, and y/x=0.5 or more and 2.6 or less, z/x=0.01 or more and 10 or less, w=0 or more and 20 or less, and n/m=0.5 or more and 20 or less are satisfied.

In formula (I), examples of the alkali metals that serve as M include Na and K. These may constitute $M_2O$ component individually, or $Na_2O$ and $K_2O$, for example, may be mixed to constitute $M_2O$ component. Examples of Me include Mg, Ca, Zn, Y, Ti, Zr, and Fe. These are not specifically limited but are preferably Mg and Ca in view of the resources and safety. Further, these may be used individually, or two or more of them may be mixed, and MgO, CaO, and the like may be mixed to constitute $Me_mO_n$ component, for example.

Further, in formula (I), y/x is 0.5 or more and 2.6 or less, preferably 1.5 or more and 2.2 or less. If y/x is over 2.6, the ion exchange capacity also decreases. Further, in formula (I), if z/x is over 1.0, the ion exchange capacity decreases. The values of x, y, and z are not specifically limited, as long as the relationships as shown in the y/x ratio and the z/x ratio are satisfied. As mentioned above, when x ($M_2O$) is, for example, x' ($Na_2O$).x" ($K_2O$), x is x'+x". When z ($Me_mO_n$) component is composed of two or more compounds, the same relationship also applies to z.

Further, n/m represents the number of oxygen ions coordinated to the element concerned and is substantially selected from values, 0.5, 1.0, 1.5, and 2.0.

An alkali metal silicate represented by formula (I) has an ion exchange capacity of 100 $CaCO_3$ mg/g or more, preferably 200 to 600 $CaCO_3$ mg/g, and is one of materials having an ion trapping capacity in the present invention.

(C1-2) aluminosilicates may be either crystalline or amorphous, but crystalline aluminosilicates are preferable as compounds having high divalent metal ion exchange/trapping capacity. Crystalline aluminosilicates are generally called zeolites, and examples thereof include those represented by formula (II) below:

$$a'(M_2O).Al_2O_3.b'(SiO_2).w(H_2O) \tag{II}$$

where M represents an alkali metal atom, a', b', and w each represent the number of moles in each component, 0.7≤a'≤1.5 and 0.8≤b'<6 are generally satisfied, and w is any positive number. Among them, those represented by formula (III) below are preferable:

$$Na_2O.Al_2O_3.n(SiO_2).w(H_2O) \tag{III}$$

where n represents 1.8 to 3.0, and w represents 1 to 6.

As the crystalline aluminosilicates (zeolites), synthetic zeolites having an average primary particle size of 0.1 to 10 μm that are typified by zeolites type A, type X, and type P are suitably used. Zeolites may be blended as powder and/or dry particles of zeolite aggregate obtained by drying zeolite slurry.

Examples of counter ions forming the salts of (C1-3) tripolyphosphates include ions selected from sodium ions and potassium ions. That is, examples of (C1-3) include a compound selected from sodium tripolyphosphate and potassium tripolyphosphate.

[(C2) Metal Ion Chelating Agents that are Organic Compounds]

Examples of (C2) metal ion chelating agents that are organic compounds include one or more organic compounds selected from (C2-1) di- or higher and tetra- or lower valent carboxylic acids or salts thereof free from amino groups and having 4 or more and 12 or less carbons, (C2-2) di- or higher and tetra- or lower valent carboxylic acids or salts thereof containing an amino group and having 4 or more and 10 or less carbons, and (C2-3) compounds having a phosphonate group or a salt thereof in the molecule.

Specifically, examples of the di- or higher and tetra- or lower valent carboxylic acids or salts thereof free from amino groups and having 4 or more and 12 or less carbons that serve as component (C2-1) include one or more carboxylic acids selected from citric acid, tartaric acid, succinic acid, and malic acid, or salts thereof.

Specifically, examples of the di- or higher and tetra- or lower valent carboxylic acids or salts thereof containing an amino group and having 4 or more and 12 or less carbons that serve as component (C2-2) include one or more carboxylic acids selected from nitrilotriacetic acid, ethylenediaminetetraacetic acid, 3-hydroxy-2,2'-iminodisuccinic acid, diethylenetriaminepentaacetic acid, and hydroxymethyl ethylenediamine triacetic acid, or salts thereof.

Examples of (C2-3) compounds having a phosphonate group or a salt thereof in the molecule include organic phosphonic acid derivatives such as ethane-1,1-diphosphonic acid, ethane-1,1,2-triphosphonic acid, 1-hydroxyethylidene-1,1-diphosphonic acid, ethane hydroxy-1,1,2-triphosphonic acid, ethane-1,2-dicarboxy-1,2-diphosphonic acid, methane hydroxy phosphonic acid, nitrilotrimethylenephosphonic acid, and ethylenediamine tetrakismethylenephosphonic acid.

As the salts of component (C2-1) to component (C2-3), alkali metal salts such as Na and K, alkanol amines having 2 to 6 carbons such as monoethanolamine, diethanolamine, and triethanolamine are preferably used in view of the versatility.

The finishing agent composition for textile products, particularly, the softening agent composition for textile products according to the present invention exerts a more excellent effect of imparting softness, particularly when it is used for softening with water containing hardness components. Therefore, the content of component (C) in the composition can be reduced. From this viewpoint, in the finishing agent composition for textile products, particularly, the softening agent composition for textile products according to the present invention, the content of component (C) is preferably 20% by mass or less, more preferably 15% by mass or less, further preferably 10% by mass, furthermore preferably 5% by mass or less. The content of component (C) is preferably 0% by mass or more. In the finishing agent composition for textile products, particularly, the softening agent composition for textile products according to the present invention, the content of component (C) may be 0% by mass. In the finishing agent composition for textile products, particularly, the softening agent composition for textile products according to the present invention, the content of component (C) is more preferably 1 mg/kg or more, further preferably 10 mg/kg or more, particularly in that the reduction in softness can be suppressed, even if the textile products are repeatedly washed or finished with water having a high content of hardness components.

<Component (D)>

The finishing agent composition for textile products, particularly, the softening agent composition for textile products according to the present invention can contain, as component (D), a surfactant other than component (A), that is, a surfactant other than the internal olefin sulfonate having 17 or more and 24 or less carbons within a range where the effects of the present invention is not prevented.

Examples of component (D) include one or more surfactants selected from component (d1), component (d2), component (d3), component (d4), and component (d5) described below.

Component (d1): Alkyl or alkenyl sulfate
Component (d2): Polyoxyalkylene alkyl or alkenyl ether sulfate having an alkyleneoxy group
Component (d3): Anionic surfactants having a sulfonate group (provided that component (A) is excluded)
Component (d4): Fatty acids or salts thereof
Component (d5): Nonionic surfactants having at least one group selected from a hydroxyl group and a polyoxyalkylene group More specifically, examples of component (d1) include one or more anionic surfactants selected from alkyl sulfate with an alkyl group having 10 or more and 18 or less carbons, and alkenyl sulfate with an alkenyl group having 10 or more and 18 or less carbons. For further enhancing the effect of softening the textile products, component (d1) is preferably one or more anionic surfactants selected from alkyl sulfates with an alkyl group having 14 or more and 18 or less carbons, more preferably one or more anionic surfactants selected from sodium alkyl sulfates with an alkyl group having 14 or more and 18 or less carbons.

More specifically, examples of component (d2) include one or more anionic surfactants selected from polyoxyalkylene alkyl sulfate with an alkyl group having 10 or more and 18 or less carbons and an average number of added moles of alkylene oxide of 1 or more and 3 or less, and polyoxyalkylene alkenyl ether sulfate with an alkenyl group having 10 or more and 18 or less carbons and an average number of added moles of alkylene oxide of 1 or more and 3 or less. For further enhancing the dispersibility of component (A) in water, component (d2) is preferably polyoxyethylene alkyl sulfates with an average number of added moles of ethylene oxide of 1 or more and 2.2 or less, more preferably polyoxyethylene alkyl sulfates with an average number of added moles of ethylene oxide of 1 or more and 2.2 or less and an alkyl group having 12 or more and 14 or less carbons, further preferably sodium salts of these.

The anionic surfactants having a sulfonate group that serve as component (d3) mean anionic surfactants having a sulfonate as a hydrophilic group.

More specifically, examples of component (d3) include one or more anionic surfactants selected from alkylbenzene sulfonates with an alkyl group having 10 or more and 18 or less carbons, alkenylbenzene sulfonates with an alkenyl group having 10 or more and 18 or less carbons, alkane sulfonates with an alkyl group having 10 or more and 18 or less carbons, α-olefin sulfonates with an α-olefin moiety having 10 or more and 18 or less carbons, α-sulfofatty acid salts with a fatty acid moiety having 10 or more and 18 or less carbons, α-sulfofatty acid lower alkyl ester salts with a fatty acid moiety having 10 or more and 18 or less carbons and an ester moiety having 1 or more and 5 or less carbons, and internal olefin sulfonates having 12 or more and 16 or less carbons. For further enhancing the effect of softening the textile products, component (d3) is preferably alkylbenzene sulfonates with an alkyl group having 11 or more and 16 or less carbons, more preferably sodium alkylbenzene sulfonates with an alkyl group having 11 or more and 16 or less carbons.

Examples of the fatty acids or salts thereof that serve as component (d4) include fatty acids or salts thereof having 10 or more and 20 or less carbons. For further enhancing the effect of softening the textile products by component (A), component (d4) has 10 or more, preferably 12 or more, more preferably 14 or more, and 20 or less, preferably 18 or less carbons.

As the salts of the anionic surfactants that are component (d1) to component (d4), alkali metal salts are preferable, sodium salts or potassium salts are more preferable, and sodium salts are further preferable.

Component (d5) is nonionic surfactants having at least one group selected from a hydroxyl group and a polyoxyalkylene group. By containing component (d5), the effect of finishing the textile products, particularly, the effect of softening the textile products by component (A) can be maintained, and a refreshing texture can be imparted to the textile products. Component (d5) is preferably nonionic surfactants having a polyoxyalkylene group and having an HLB of 7 or more. Nonionic surfactants having an HLB of preferably 8 or more, more preferably 9 or more, further preferably 10 or more, furthermore preferably over 10.5, are preferable, in that the effect of finishing, particularly, softening the textile products by component (A) can be maintained. The HLB of component (d5) is 11 or more, is preferably 12 or more, more preferably 13 or more, more preferably 14 or more, more preferably 15 or more, more preferably 16 or more, and 20 or less, in that the effect of softening the textile products by component (A) can be maintained. The value of HLB in the present invention is determined by the method of Kunieda, et al. described in "Journal of Colloid and Interface Science, Vol. 107. No. 1, September 1985". The method according to this literature is a method for determining HLB based on the finding that a specific temperature ($T_{HLB}$) and an HLB value by Griffin have a linear relationship.

More specific examples of component (d5) include nonionic surfactants having an HLB of preferably 7 or more, more preferably 8 or more, further preferably 9 or more, furthermore preferably 10 or more, furthermore preferably over 10.5 and represented by formula (d5) below:

$$R^1(CO)_mO\text{-}(A^1O)_n\text{--}R^2 \quad (d5)$$

where $R^1$ is an aliphatic hydrocarbon group having 9 or more and 16 or less carbons, $R^2$ is a hydrogen atom or a methyl group, CO is a carbonyl group, m is 0 or 1, the $A^1O$ group is one or more groups selected from an ethyleneoxy group and a propyleneoxy group, and n is an average number of added moles, and is 6 or more and 50 or less.

In formula (d5), $R^1$ is an aliphatic hydrocarbon group having 9 or more and 16 or less carbons. As the number of carbons in $R^1$ increases, the HLB value decreases, while the HLB value increases as the number of carbons in $R^1$ decreases. For further facilitating removal of stains present in the textile products, $R^1$ has 9 or more, preferably 10 or more, more preferably 11 or more carbons. For further enhancing the effect of softening the textile products, $R^1$ has 16 or less, preferably 15 or less, more preferably 14 or less carbons.

Examples of the aliphatic hydrocarbon group represented by $R^1$ include a group selected from an alkyl group and an alkenyl group.

In formula (d5), the $A^1O$ group is one or more groups selected from an ethyleneoxy group and a propyleneoxy group. In the case of containing an ethyleneoxy group and a propyleneoxy group, the ethyleneoxy group and the propyleneoxy group may be bound through either block binding or random binding. The $A^1O$ group is preferably a group containing an ethyleneoxy group, in that the effect of softening the textile products by component (A) is hardly inhibited. The ethyleneoxy group has a higher HLB value than the propyleneoxy group.

In formula (d5), n is an average number of added moles, and is 6 or more and 50 or less. As the number of n increases, the HLB value increases, while the HLB value decreases as the number of n decreases. The value of n is 6 or more, preferably 6.5 or more, more preferably 7 or more, more preferably 8 or more, more preferably 9 or more, more preferably 10 or more, more preferably 12 or more, and 50 or less, in that the effect of softening the textile products by component (A) is hardly inhibited.

When the finishing agent composition for textile products, particularly, the softening agent composition for textile products according to the present invention contains component (D), the content of component (D) is preferably 0.1% by mass or more, more preferably 0.5% by mass or more, further preferably 1% by mass or more, and preferably 10% by mass or less, more preferably 9% by mass or less, further preferably 8% by mass or less, for further enhancing the dispersibility of component (A) in water.

Further, in the finishing agent composition for textile products, particularly, the softening agent composition for textile products according to the present invention, the mass ratio (D)/(A) of the content of component (D) to the content of component (A) is preferably 1.5 or less, more preferably 1.2 or less, further preferably 1 or less, furthermore preferably 0.8 or less, furthermore preferably 0.6 or less, furthermore preferably 0.5 or less, furthermore preferably 0.4 or less, furthermore preferably 0.3 or less, furthermore preferably 0.2 or less, furthermore preferably 0.1 or less, in that the effect of softening the textile products by component (A) is hardly inhibited. The mass ratio (D)/(A) of the content of component (D) to the content of component (A) may be 0.

<Component (E)>

The finishing agent composition for textile products, particularly, the softening agent composition for textile products according to the present invention can contain an organic solvent having one or more hydroxyl groups as component (E). Examples of the organic solvent having one or more hydroxyl groups include one or more organic solvents selected from mono- or higher and hexa- or lower valent alcohols with an aliphatic hydrocarbon group having 2 or more and 6 or less carbons, such as ethanol, 1-propanol, 2-propanol, ethylene glycol, propylene glycol, butylene glycol, 2-methyl-2,4-pentanediol, 1,5-pentanediol, 1,6-hexanediol, glycerin, and 2-methyl-2,4-pentanediol.

When the finishing agent composition for textile products, particularly, the softening agent composition for textile products according to the present invention contains component (E), the content of component (E) is preferably 0.5% by mass or more, more preferably 1% by mass or more, further preferably 2% by mass or more, and preferably 30% by mass or less, more preferably 25% by mass or less, further preferably 20% by mass or less, for further enhancing the effect of softening the textile products, even if the temperature of the treatment liquid for textile products obtained from the finishing agent composition for textile products, particularly, the softening agent composition for textile products containing component (A) and water is low.

<Water>

The finishing agent composition for textile products, particularly, the softening agent composition for textile products according to the present invention preferably contains water. Water is used for rendering the composition mainly at 4° C. to 40° C. into liquid form. Deionized water (which may be referred to also as ion-exchanged water) or water obtained by adding sodium hypochlorite to ion-exchanged water in an amount of 1 mg/kg or more and 5 mg/kg or less can be used as the water. Further, tap water also can be used.

<Method for Finishing, Particularly, Method for Softening Textile Product>

The present invention discloses a method for finishing textile products, the method including contacting the textile products with a treatment liquid for textile products containing water and an internal olefin sulfonate having 17 or more and 24 or less carbons in an amount of 0.002% by mass or more and 6% by mass or less relative to the textile products. This method is a method for finishing textile products with a treatment liquid for textile products containing water and an internal olefin sulfonate having 17 or more and 24 or less carbons in an amount of 0.002% by mass or more and 6% by mass or less relative to the textile products.

Examples of the method for finishing textile products according to the present invention include a method for softening textile products, the method including contacting the textile products with a treatment liquid for textile products containing water and an internal olefin sulfonate having 17 or more and 24 or less carbons in an amount of 0.002% by mass or more and 6% by mass or less relative to the textile products. This method is a method for softening textile products with a treatment liquid for textile products containing water and an internal olefin sulfonate having 17 or more and 24 or less carbons in an amount of 0.002% by mass or more and 6% by mass or less relative to the textile products.

The internal olefin sulfonate having 17 or more and 24 or less carbons used in the method for treating textile products according to the present invention means the same as component (A). Specific examples and preferable aspects of component (A) are the same as in the finishing agent composition for textile products, particularly, the softening agent composition for textile products according to the present invention.

In the method for finishing textile products, particularly, the method for softening textile products according to the present invention, the water used in the treatment liquid for textile products is preferably water containing hardness components, in that the softness of the textile products can be improved. Examples of the water containing hardness components include water having a German hardness of 1° DH or more and 30° DH or less.

Here, the German hardness (° dH) in the present description means the concentration of calcium and magnesium in water expressed as 1 mg/L (ppm) as a concentration calculated in terms of $CaCO_3$=about 0.056° dH (1° dH=17.8 ppm).

The concentration of calcium and magnesium for such a German hardness is determined by the chelate titration method using ethylenediaminetetraacetic acid disodium salt.

A specific method for determining the German hardness of water in the present description will be described below.
<Method for Determining German Hardness of Water>
[Reagent]

0.01 mol/l EDTA.2Na solution: 0.01 mol/l aqueous solution of disodium ethylenediaminetetraacetate (titration solution, 0.01 M EDTA-Na2, manufactured by Sigma-Aldrich Corporation (SIGMA-ALDRICH))

Universal BT indicator (product name: Universal BT, manufactured by DOJINDO LABORATORIES)

Ammonia buffer for hardness determination (solution obtained by dissolving 67.5 g of ammonium chloride in 570 ml of 28 w/v % ammonia water and adjusting the total amount to 1000 ml with ion-exchanged water)
[Determination of Hardness]
(1) Collect 20 ml of water as a sample into a conical beaker with a hole pipette.
(2) Add 2 ml of an ammonia buffer for hardness determination thereto.
(3) Add 0.5 ml of a Universal BT indicator thereto. Confirm that the solution after the addition is red purple.
(4) Add a 0.01 mol/l EDTA.2Na solution dropwise from a burette while shaking the conical beaker well, and stop titration upon discoloration of water as a sample into blue.
(5) Determine the total hardness by the calculation formula below:

Hardness (° dH)=$T \times 0.01 \times F \times 56.0774 \times 100/A$

T: Titer (mL) of 0.01 mol/l EDTA.2Na solution
A: Sample volume (20 mL, volume of water as a sample)
F: Factor of 0.01 mol/l EDTA.2Na solution The treatment liquid for textile products used in the method for finishing textile products, particularly, the method for softening textile products according to the present invention can be obtained by mixing the finishing agent composition for textile products, particularly, the softening agent composition for textile products according to the present invention with water. The treatment liquid for textile products can contain components (B) to (E) and other optional components other than component (A).

In the method for finishing textile products, particularly, the method for softening textile products according to the present invention, textile products are contacted with a treatment liquid for textile products containing water and an internal olefin sulfonate having 17 or more and 24 or less carbons in an amount of 0.002% by mass or more and 6% by mass or less relative to the textile products. The content of the internal olefin sulfonate having 17 or more and 24 or less carbons in the treatment liquid for textile products is preferably 0.004% by mass or more, more preferably 0.008% by mass or more, further preferably 0.01% by mass or more, furthermore preferably 0.1% by mass or more, and preferably 5% by mass or less, more preferably 4% by mass or less, further preferably 3% by mass or less.

In the treatment liquid for textile products used in the method for finishing textile products, particularly, the method for softening textile products according to the present invention, the concentration of the internal olefin sulfonate having 17 or more and 24 or less carbons that is component (A) is preferably 10 mg/kg or more, more preferably 20 mg/kg or more, further preferably 30 mg/kg or more, furthermore preferably 40 mg/kg or more, and preferably 1000 mg/kg or less, more preferably 900 mg/kg or less, further preferably 800 mg/kg or less. It is preferable to contact the textile products with the treatment liquid for textile products containing component (A) at the above concentration in an amount such that the mass of component (A) is 0.002% by mass or more and 6% by mass or less relative to the mass of the textile products.

In the treatment liquid for textile products used in the method for finishing textile products, particularly, the method for softening textile products according to the present invention, the content of an internal olefin sulfonate having 16 or less carbons is preferably 90 parts by mass or less, more preferably 80 parts by mass or less, further preferably 70 parts by mass or less, furthermore preferably 60 parts by mass or less, furthermore preferably 50 parts by mass or less, furthermore preferably 40 parts by mass or less, furthermore preferably 30 parts by mass or less, furthermore preferably 20 parts by mass or less, furthermore preferably 10 parts by mass or less, relative to a content of component (A) of 100 parts by mass. In the treatment liquid for textile products used in the method for finishing textile products, particularly, the method for softening textile products according to the present invention, the content of the internal olefin sulfonate having 16 or less carbons is preferably 0 parts by mass relative to a content of component (A) of 100 parts by mass, that is, the internal olefin sulfonate having 16 or less carbons is preferably not contained.

The temperature of the treatment liquid for textile products used in the method for finishing, particularly, softening textile products is preferably 0° C. or more, preferably 3° C. or more, more preferably 5° C. or more, so as to be capable of further improving the softness of the textile products. Further, the temperature of the treatment liquid for textile products is preferably 40° C. or less, more preferably 35° C. or less, so as to be capable of finishing the textile products with more softness.

In recent years, there has been a tendency that the size of washing machines increases, and the value of the bath ratio represented by the ratio of the water volume (liter) of the treatment liquid for textile products to the mass (kg) of clothing, that is, the water volume (liter) of the treatment liquid for textile products/the mass (kg) of clothing (hereinafter, this ratio may be referred to as bath ratio) decreases. In the case of using a domestic washing machine, a reduction in bath ratio may cause an increase in abrasion between fibers due to stirring during finishing, particularly, softening the textile products, as a result of which the softness of the textile products may be impaired. The method for finishing textile products, particularly, the method for softening textile products according to the present invention can finish fibers with softness even under the conditions of finishing, particularly, softening textile products with a low bath ratio. For finishing fibers with softness, the bath ratio is preferably 2 or more, further preferably 3 or more, more preferably 4 or more, more preferably 5 or more. Further, it is possible to finish textile products with softness even with a bath ratio of 60 or less, further 55 or less, further 50 or less, further 45 or less, further 40 or less, further 30 or less, further 20 or less.

The method for finishing textile products, particularly, the method for softening textile products according to the present invention can finish textile products with more softness even if the finishing time, particularly, the softening time for the textile products is short. The finishing time, particularly, the softening time for the textile products is preferably 1 minute or more, preferably 2 minutes or more, and preferably 1 hour or less, more preferably 30 minutes or less, more preferably 20 minutes or less, more preferably 15 minutes or less, so as to be capable of finishing the textile products with more softness.

Examples of a method for contacting the textile products with the treatment liquid for textile products in the method for finishing textile products, particularly, the method for softening textile products according to the present invention include a method of immersing the textile products in the treatment liquid for textile products, or a method of finishing, particularly, softening the textile products by stirring the textile products together with the treatment liquid for textile products. As a device used for the stirring, a washing machine, for example, can be used. Accordingly, the method of softening the textile products by stirring the textile products together with the treatment liquid for textile products is preferable in the present invention, for finishing the textile products with more softness. Specifically, examples of the washing machine include drum washing machines, pulsator washing machines, or agitator washing machines. Washing machines that are commercially available for domestic use can be used as these rotary washing machines.

The method for finishing textile products, particularly, the method for softening textile products according to the present invention can be incorporated into a washing process of textile products.

The present invention provides a method for treating textile products, the method including: step 1 of washing the textile products with a washing liquid containing one or more surfactants [which may be hereinafter referred to as component (F)] selected from anionic surfactants and nonionic surfactants; and step 2 of contacting the textile products after step 1 with a treatment liquid for textile products containing water and an internal olefin sulfonate having 17 or more and 24 or less carbons in an amount of 0.002% by mass or more and 6% by mass or less relative to the textile products.

The matters described for the finishing agent composition for textile products, particularly, the softening agent composition for textile products according to the present invention and for the method for finishing textile products, particularly, the method for softening textile products can be appropriately applied to the aforementioned method.

Step 1 can be carried out according to normal washing of textile products.

Step 2 preferably includes performing the finishing method, particularly, the softening method of the present invention mentioned above.

As described above, in a process of washing textile products that includes softening, the textile products are generally washed, rinsed, and softened. Conventionally, detergents mainly containing anionic surfactants have been mostly used for washing, and softeners containing cationic surfactants have been mostly used for softening. However, a short rinse time or a small amount of water used for rinsing may result in insufficient rinsing, so that the anionic surfactants used for washing are carried into the treatment bath for softening, thereby counteracting the effects of cationic surfactants, in some cases. Further, detergents mainly containing nonionic surfactants are also known, but insufficient rinsing may cause hard texture of textile products in some cases, even if softening is performed. When the method for finishing textile products, particularly, the method for softening textile products according to the present invention is incorporated into a washing process, a sufficient softness can be imparted to the textile products, and the original water absorbency of the textile products can be maintained, even if the rinsing after step 1 is insufficient. In other words, the washing process of textile products according to the present invention can reduce the amount of water used in the rinsing step. Further, since the time required for rinsing can be reduced, the time required for the washing process of textile products also can be reduced. Further, regardless of the composition of the detergent used in step 1, a sufficient softness can be imparted to the textile products, and the original water absorbency of the textile products can be maintained. Therefore, the operator can enjoy an advantage of wider choices of detergents.

Step 1 is a step of washing textile products with a washing liquid containing component (F).

In component (F), examples of the anionic surfactants include one or more anionic surfactants selected from component (f1), component (f2), component (f3), and component (f4) described below. In component (F), examples of the nonionic surfactants include one or more nonionic surfactants selected from component (f5) described below.

Component (f1): Alkyl or alkenyl sulfate
Component (f2): Polyoxyalkylene alkyl or alkenyl ether sulfate having an alkyleneoxy group
Component (f3): Anionic surfactants having a sulfonate group
Component (f4): Fatty acids or salts thereof
Component (f5): Nonionic surfactants having at least one group selected from a hydroxyl group and a polyoxyalkylene group More specifically, examples of component (f1) include one or more anionic surfactants selected from alkyl sulfate with an alkyl group having 10 or more and 18 or less carbons, and alkenyl sulfate with an alkenyl group having 10 or more and 18 or less carbons.

More specifically, examples of component (f2) include one or more anionic surfactants selected from polyoxyalkylene alkyl sulfate with an alkyl group having 10 or more and 18 or less carbons and an average number of added moles of alkylene oxide of 1 or more and 3 or less, and polyoxyalkylene alkenyl ether sulfate with an alkenyl group having 10 or more and 18 or less carbons and an average number of added moles of alkylene oxide of 1 or more and 3 or less.

The anionic surfactants having a sulfonate group that serve as component (f3) mean anionic surfactants having a sulfonate as a hydrophilic group.

More specifically, examples of component (f3) include one or more anionic surfactants selected from alkylbenzene sulfonates with an alkyl group having 10 or more and 18 or less carbons, alkenylbenzene sulfonates with an alkenyl group having 10 or more and 18 or less carbons, alkane sulfonates with an alkyl group having 10 or more and 16 or less carbons, α-olefin sulfonates with an α-olefin moiety having 10 or more and 16 or less carbons, α-sulfofatty acid salts with a fatty acid moiety having 10 or more and 18 or less carbons, α-sulfofatty acid lower alkyl ester salts with a fatty acid moiety having 10 or more and 18 or less carbons and an ester moiety having 1 or more and 5 or less carbons, and internal olefin sulfonates having 12 or more and 16 or less carbons.

Examples of the fatty acids or salts thereof that serve as component (f4) include fatty acids having 10 or more and 20 or less carbons or salts thereof.

Examples of the salts of the anionic surfactants that serve as component (f1) to component (f4) include alkali metal salts and alkanol ammonium salts having 1 or more and 6 or less carbons. Examples of the alkali metal salts include sodium salts or potassium salts. Examples of the alkanol ammonium salts having 1 or more and 6 or less carbons include monoethanol ammonium salt, diethanol ammonium salt, triethanol ammonium salt, N-methyl monoethanol ammonium salt, N-methyl diethanol ammonium salt, and N-methyl triethanol ammonium salt.

Component (f5) is nonionic surfactants having at least one group selected from a hydroxyl group and a polyoxyalkylene group. Examples of the oxyalkylene group include oxyalkylene groups having 2 or more and 3 or less carbons. For further enhancing the effect of washing the textile products, the oxyalkylene group having 2 carbons is preferably an oxyethylene group, and the oxyalkylene group having 3 carbons is preferably an oxypropylene group. Component (f5) is preferably nonionic surfactants having an HLB of over 7, for further enhancing the detergency. The HLB of component (f5) is preferably 8 or more, more preferably 9 or more, and 18 or less, in that the effect of washing the textile products is further enhanced. The value of HLB in the present invention is determined by the method of Kunieda, et al. described in "Journal of Colloid and Interface Science, Vol. 107. No. 1, September 1985". This literature discloses a method for determining HLB based on the finding that a specific temperature ($T_{HLB}$) and an HLB value by Griffin have a linear relationship.

More specific examples of component (f5) include nonionic surfactants having an HLB of over 7 and represented by formula (f5) below:

$$R^3(CO)_mO\text{-}(A^2O)_n\text{---}R^4 \quad (f5)$$

where $R^3$ is an aliphatic hydrocarbon group having 9 or more and 18 or less carbons, $R^4$ is a hydrogen atom or a methyl group, CO is a carbonyl group, m is a 0 or 1, the $A^2O$ group is one or more groups selected from an ethyleneoxy group and a propyleneoxy group, and n is an average number of added moles, and is 3 or more and 50 or less.

In formula (f5), $R^3$ is an aliphatic hydrocarbon group having 9 or more and 18 or less carbons. As the number of carbons in $R^3$ increases, the HLB value decreases, while the HLB value increases as the number of carbons in $R^3$ decreases. For further facilitating removal of stains present in the textile products, the number of carbons in $R^3$ is 9 or more, preferably 10 or more, more preferably 11 or more, and is 18 or less, preferably 16 or less, more preferably 15 or less, further preferably 14 or less.

Examples of the aliphatic hydrocarbon group represented by $R^3$ include a group selected from an alkyl group and an alkenyl group.

In formula (f5), the $A^2O$ group is one or more groups selected from an ethyleneoxy group and a propyleneoxy group. In the case of containing an ethyleneoxy group and a propyleneoxy group, the ethyleneoxy group and the propyleneoxy group may be bound through either block binding or random binding. The $A^2O$ group is preferably a group containing an ethyleneoxy group, in that the effect of softening the textile products by component (A) is hardly inhibited. The ethyleneoxy group has a higher HLB value than the propyleneoxy group.

In formula (f5), n is an average number of added moles, and is 3 or more and 50 or less. As the number of n increases, the HLB value increases, while the HLB value decreases as the number of n decreases. For achieving higher detergency to textile products, n is 3 or more, preferably 4 or more, more preferably 5 or more, more preferably 6 or more, and is 50 or less, preferably 45 or less, more preferably 40 or less, more preferably 35 or less, more preferably 26 or less, further preferably 24 or less.

The washing liquid used in step 1 can be obtained by mixing one or more surfactants selected from anionic surfactants and nonionic surfactants that serve as component (F) with water. Examples of the water include ion-exchanged water and water containing hardness components. As the water containing hardness components, the same water containing hardness components as used in the softening method can be used.

In the washing liquid used in step 1 for textile products according to the present invention, the concentration of component (F) is preferably 5 mg/kg or more and 10000 mg/kg or less. The concentration is more preferably 10 mg/kg or more, further preferably 30 mg/kg or more, and more preferably 5000 mg/kg or less, further preferably 1000 mg/kg or less.

The washing liquid used in step 1 for textile products according to the present invention can contain components blended into detergents for textile products such as builders, perfumes, pigments.

For achieving higher detergency to textile products, the temperature of the washing liquid used in step 1 is preferably 0° C. or more, preferably 3° C. or more, more preferably 5° C. or more, and preferably 40° C. or less, more preferably 35° C. or less.

In recent years, there has been a tendency that the size of washing machines increases, and the value of the bath ratio represented by the ratio of the water volume (liter) of the washing liquid in step 1 to the mass (kg) of clothing, that is, the water volume (liter) of the washing liquid in step 1/the mass (kg) of clothing (hereinafter, this ratio may be referred to as washing bath ratio) decreases. In the case of using a domestic washing machine, a reduction in washing bath ratio may cause an increase in abrasion between fibers due to stirring in step 1, as a result of which the softness of the textile products may be impaired. For finishing fibers with more softness, the washing bath ratio is preferably 2 or more, further preferably 3 or more, more preferably 4 or more, more preferably 5 or more. Further, textile products can be finished with softness even with a washing bath ratio of 45 or less, further 40 or less, further 30 or less, further 20 or less.

In step 1 of the present invention, the washing time is preferably 1 minute or more, preferably 2 minutes or more, and preferably 1 hour or less, more preferably 30 minutes or less, more preferably 20 minutes or less, more preferably 15 minutes or less, for improving the detergency to the textile products.

Examples of a method for contacting the textile products with the washing liquid in step 1 of the present invention include a method of immersing the textile products in the washing liquid, or a method for washing the textile products by stirring the textile products together with the washing liquid. As a device used for the stirring, a washing machine, for example, can be used. Specifically, examples of the washing machine include drum washing machines, pulsator washing machines, or agitator washing machines. Washing machines that are commercially available for domestic use can be used as these rotary washing machines.

Step 1 can be carried out multiple times.

Step 1 preferably has a step of rinsing, with water, the textile products after washing (which may be hereinafter referred to as rinsing step). The water to be used in the rinsing step may be the same as in step 1.

In the present invention, the step of rinsing the textile products with water means a step of reducing the amount of anionic surfactants and nonionic surfactants present in the textile products obtained in step 1.

Examples of the rinsing step include a method of contacting the textile products washed in step 1 with fresh water.

In the rinsing step, the value of the bath ratio represented by the ratio of the mass of the textile products (kg) before undergoing step 1 to the volume of water (liter), that is, the volume of water (liter) used for rinsing/the mass of the textile products (kg) (this ratio may be hereinafter referred to as rinsing bath ratio) is preferably 2 or more, more preferably 3 or more, further preferably 4 or more, furthermore preferably 5 or more, and preferably 45 or less, more preferably 40 or less, further preferably 30 or less, furthermore preferably 20 or less, in that the effect of imparting a texture to the textile products in step 2 can be further improved. The rinsing step can be carried out multiple times.

The method for treating textile products according to the present invention can include a dehydration step of dehydrating the textile products, and a drying step of drying the textile products, other than step 1, step 2, and the rinsing step.

<Aspects of the Present Invention>

More specific examples of the aspects of the present invention will be shown below. The matters described for the fiber modifier, the finishing agent composition for textile products, the method for finishing textile products, the method for treating textile products, and the use according to the present invention can be appropriately applied to the following aspects.

<1> A fiber modifier composed of an internal olefin sulfonate having 17 or more and 24 or less carbons.

<2> The fiber modifier according to <1>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

<3> The fiber modifier according to <2>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.

<4> The fiber modifier according to any one of <1> to <3>, wherein the internal olefin sulfonate having 17 or more and 24 or less carbons has preferably 18 or more, and preferably 22 or less, more preferably 20 or less, further preferably 19 or less carbons.

<5> The fiber modifier according to any one of <1> to <4>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.

<6> The fiber modifier according to any one of <1> to <5>, wherein a content of 1-olefin sulfonate in the internal olefin sulfonate having 17 or more and 24 or less carbons is 10% by mass or less.

<7> A finishing agent composition for textile products, containing a fiber modifier composed of an internal olefin sulfonate having 17 or more and 24 or less carbons.

<8> The finishing agent composition for textile products according to <7>, wherein a content of 1-olefin sulfonate in the internal olefin sulfonate having 17 or more and 24 or less carbons is 10% by mass or less.

<9> The finishing agent composition for textile products according to <7> or <8>, further containing a polyvalent metal salt.

<10> The finishing agent composition for textile products according to <9>, wherein the polyvalent metal salt is one or more polyvalent metal salts selected from inorganic polyvalent metal salts and organic polyvalent metal salts.

<11> The finishing agent composition for textile products according to <10>, wherein the inorganic polyvalent metal salts are one or more inorganic polyvalent metal salts selected from inorganic divalent metal salts and inorganic trivalent metal salts, and the organic polyvalent metal salts are one or more organic polyvalent metal salts selected from organic divalent metal salts and organic trivalent metal salts.

<12> The finishing agent composition for textile products according to <11>, wherein the inorganic divalent metal salts are one or more inorganic divalent metal salts selected from calcium salts and magnesium salts, and the inorganic trivalent metal salts are aluminum salts.

<13> The finishing agent composition for textile products according to <11>, wherein the organic polyvalent metal salts are preferably organic polyvalent metal salts having 1 or more and 8 or less carbons, more preferably one of more organic polyvalent metal salts selected from sulfonic acid polyvalent metal salts having 1 or more and 8 or less carbons, sulfate ester polyvalent metal salts having 1 or more and 8 or less carbons, and carboxylic acid polyvalent metal salts having 1 or more and 8 or less carbons.

<14> The finishing agent composition for textile products according to any one of <10> to <13>, wherein the content of the polyvalent metal salts in the finishing agent composition for textile products is 10 mg/kg or more, more preferably 20 mg/kg or more, further preferably 30 mg/kg or more, and preferably 20% by mass or less, more preferably 15% by mass or less, further preferably 10% by mass or less.

<15> The finishing agent composition for textile products according to any one of <7> to <14>, wherein a content of a metal ion chelating agent in the finishing agent composition for textile products is 0% by mass or more and 20% by mass or less.

<16> The finishing agent composition for textile products according to <15>, wherein the metal ion chelating agent is one or more metal ion chelates, which are (C1) inorganic compounds, selected from (C1-1) alkali metal silicates, (C1-2) aluminosilicates, and (C1-3) tripolyphosphates.

<17> The finishing agent composition for textile products according to <15>, wherein the metal ion chelating agent is one or more metal ion chelating agents, which are (C2) organic compounds, selected from (C2-1) di- or higher and tetra- or lower valent carboxylic acids or salts thereof free from amino groups and having 4 or more and 12 or less carbons, (C2-2) di- or higher and tetra- or lower valent carboxylic acids or salts thereof containing an amino group and having 4 or more and 10 or less carbons, and (C2-3) compounds having a phosphonate group or a salt thereof in the molecule.

<18> The finishing agent composition for textile products according to any one of <15> to <17>, wherein a content of the metal ion chelating agent is 20% by mass or less, preferably 15% by mass or less, more preferably 10% by mass, further preferably 5% by mass or less, and is 1 mg/kg or more, preferably 10 mg/kg or more.

<19> The finishing agent composition for textile products according to any one of <7> to <18>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

<20> The finishing agent composition for textile products according to <19>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.

<21> The finishing agent composition for textile products according to any one of <7> to <20>, wherein the internal olefin sulfonate having 17 or more and 24 or less carbons has preferably 18 or more, and preferably 22 or less, more preferably 20 or less, further preferably 19 or less carbons.

<22> The finishing agent composition for textile products according to any one of <7> to <21>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.

<23> The finishing agent composition for textile products according to any one of <7> to <22>, further containing a nonionic surfactant having at least one group selected from a hydroxyl group and a polyoxyalkylene group.

<24> The finishing agent composition for textile products according to <23>, wherein the nonionic surfactant is a nonionic surfactant having a polyoxyalkylene group and an HLB of 7 or more.

<25> The finishing agent composition for textile products according to <24>, wherein the nonionic surfactant is a nonionic surfactant having an HLB of 7 or more, preferably 8 or more, more preferably 9 or more, further preferably 10 or more, furthermore preferably over 10.5, and represented by formula (d5) below:

$$R^1(CO)_mO\text{-}(A^1O)_n\text{—}R^2 \tag{d5}$$

where $R^1$ is an aliphatic hydrocarbon group having 9 or more and 16 or less carbons, $R^2$ is a hydrogen atom or a methyl group, CO is a carbonyl group, m is 0 or 1, the $A^1O$ group is one or more groups selected from an ethyleneoxy group and a propyleneoxy group, n is an average number of added moles, and is 6 or more and 50 or less.

<26> The finishing agent composition for textile products according to any one of <23> to <25>, wherein, when the internal olefin sulfonate having 17 or more and 24 or less carbons is referred to as component (A), and the nonionic surfactant is referred to as component (D), a mass ratio (D)/(A) of the content of component (D) to the content of component (A) is preferably 1.5 or less, more preferably 1.2 or less, further preferably 1 or less, furthermore preferably 0.8 or less, furthermore preferably 0.6 or less, furthermore preferably 0.5 or less, furthermore preferably 0.4 or less, furthermore preferably 0.3 or less, furthermore preferably 0.2 or less, furthermore preferably 0.1 or less, or 0.

<27> The finishing agent composition for textile products according to any one of <7> to <26>, further containing water.

<28> The finishing agent composition for textile products according to any one of <7> to <27>, wherein a finishing agent is a softening agent.

<29> A method for finishing textile products, including: contacting the textile products with a treatment liquid for textile products containing water and an internal olefin sulfonate having 17 or more and 24 or less carbons in an amount of 0.002% by mass or more and 6% by mass or less relative to the textile products.

<30> The method for finishing textile products according to <29>, wherein a content of 1-olefin sulfonate in the internal olefin sulfonate having 17 or more and 24 or less carbons is 10% by mass or less.

<31> The method for finishing textile products according to <29> or <30>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

<32> The method for finishing textile products according to <31>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.

<33> The method for finishing textile products according to any one of <29> to <32>, wherein the internal olefin sulfonate having 17 or more and 24 or less carbons has preferably 18 or more, and preferably 22 or less, more preferably 20 or less, further preferably 19 or less carbons.

<34> The method for finishing textile products according to any one of <29> to <33>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.

<35> The method for finishing textile products according to any one of <29> to <34>, wherein a content of 1-olefin sulfonate in the internal olefin sulfonate having 17 or more and 24 or less carbons is 10% by mass or less.

<36> A method for treating textile products, including: step 1 of washing the textile products with a washing liquid containing one or more surfactants selected from anionic surfactants and nonionic surfactants; and step 2 of contacting the textile products after step 1 with a treatment liquid for textile products containing water and an internal olefin sulfonate having 17 or more and 24 or less carbons in an amount of 0.002% by mass or more and 6% by mass or less relative to the textile products.

<37> The method for treating textile products according to <36>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

<38> The method for treating textile products according to <37>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.

<39> The method for treating textile products according to any one of <36> to <38>, wherein the internal olefin sulfonate having 17 or more and 24 or less carbons has preferably 18 or more, and preferably 22 or less, more preferably 20 or less, further preferably 19 or less carbons.

<40> The method for treating textile products according to any one of <36> to <39>, wherein the internal olefin sulfonate having 17 or more and 24 or less carbons contains an internal olefin sulfonic acid having 18 or more carbons in an amount of preferably 80% by mass or more, more preferably 90° by mass or more, and an internal olefin sulfonate having 20 or more and 24 or less carbons in an amount of preferably 20° by mass or less, more preferably 10° by mass or less, further preferably 5% by mass or less, furthermore preferably 3% by mass or less, furthermore preferably 1% by mass or less, furthermore preferably 0% by mass.

<41> The method for treating textile products according to any one of <36> to <40>, wherein a content of 1-olefin sulfonate in the internal olefin sulfonate having 17 or more and 24 or less carbons is 10% by mass or less.

<42> Use of an internal olefin sulfonate having 17 or more and 24 or less carbons as a fiber modifier.

<43> The use according to <42>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

<44> The use according to <43>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.

<45> The use according to <42> to <44>, wherein the internal olefin sulfonate having 17 or more and 24 or less carbons has preferably 18 or more, and preferably 22 or less, more preferably 20 or less, further preferably 19 or less carbons.

<46> The use according to any one of <42> to <45>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.

<47> The use according to any one of <42> to <46>, wherein a content of 1-olefin sulfonate in the internal olefin sulfonate having 17 or more and 24 or less carbons is 10% by mass or less.

<48> Use of an internal olefin sulfonate having 17 or more and 24 or less carbons as a finishing agent for textile products.

<49> The use according to <48>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/ (IO-2S) of (IO-1S) to (IO-2S) is 0.6 or more and 6 or less.
<50> The use according to <49>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.
<51> The use according to any one of <48> to <50>, wherein the internal olefin sulfonate having 17 or more and 24 or less carbons has preferably 18 or more, and preferably 22 or less, more preferably 20 or less, further preferably 19 or less carbons.
<52> The use according to any one of <48> to <51>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.
<53> The use according to any one of <48> to <52>, wherein a content of 1-olefin sulfonate in the internal olefin sulfonate having 17 or more and 24 or less carbons is 10% by mass or less.
<54> Use of an internal olefin sulfonate having 17 or more and 24 or less carbons as a softening agent for textile products.
<55> The use according to <54>, wherein the internal olefin sulfonate having 17 or more and 24 or less carbons contains an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/ (IO-2S) of (IO-1S) to (IO-2S) is 0.6 or more and 6 or less.
<56> The use according to <55>, wherein the mass ratio (IO-1S)/(IO-2S) of the content of (IO-1S) to the content of (IO-2S) in the internal olefin sulfonate having 17 or more and 24 or less carbons is more preferably 0.65 or more, further preferably 0.70 or more, furthermore preferably 0.75 or more, furthermore preferably 0.8 or more, furthermore preferably 1.0 or more, furthermore preferably 1.2 or more, furthermore preferably 1.4 or more, furthermore preferably 1.6 or more, furthermore preferably 2.0 or more, furthermore preferably 3.0 or more, furthermore preferably 4.0 or more, and preferably 6 or less, more preferably 5.5 or less, further preferably 5.0 or less, furthermore preferably 4.5 or less.
<57> The use according to any one of <54> to <56>, wherein the internal olefin sulfonate having 17 or more and 24 or less carbons has preferably 18 or more, and preferably 22 or less, more preferably 20 or less, further preferably 19 or less carbons.
<58> The use according to any one of <54> to <57>, wherein the internal olefin sulfonate having 17 or more and 24 or less carbons contains an internal olefin sulfonic acid having 18 or more carbons in an amount of preferably 80% by mass or more, more preferably 90% by mass or more, and an internal olefin sulfonate having 20 or more and 24 or less carbons in an amount of preferably 20% by mass or less, more preferably 10% by mass or less, further preferably 5% by mass or less, furthermore preferably 3% by mass or less, furthermore preferably 1% by mass or less, furthermore preferably 0% by mass.
<59> The use according to any one of <54> to <58>, wherein a content of 1-olefin sulfonate in the internal olefin sulfonate having 17 or more and 24 or less carbons is 10% by mass or less.

EXAMPLES

Production Examples A1 to A3

Synthesis of Internal Olefins A1 to A3 having 18 Carbons 7000 g (25.9 mol) of 1-octadecanol (product name: KALCOL 8098, manufactured by Kao Corporation) and 700 g (10% by mass relative to the raw material alcohol) of γ-alumina (STREM Chemicals, Inc.) as a solid acid catalyst were put into a flask with a stirrer, followed by reaction at 280° C. under stirring while circulating nitrogen (7000 mL/min.) in the flask and varying the reaction time. The crude internal olefins obtained were transferred to a distillation flask and distilled at 148-158° C./0.5 mmHg to obtain internal olefins A1 to A3 having 18 carbons with an olefin purity of 100%. Table 1 shows the distribution of double bonds in the internal olefins obtained.

Production Example D

Synthesis of Internal Olefin D having 16 Carbons

Internal olefin D was produced by the method of Production Example C described in JP-A 2014-76988. Table 1 shows the distribution of double bonds in the internal olefin.

TABLE 1

|  |  | Internal olefin | | | |
|---|---|---|---|---|---|
|  |  | A1 | A2 | A3 | D |
| The number of carbons in olefin | | 18 | 18 | 18 | 16 |
| Composition in olefin (% by mass) | Linear olefin | 99.8 | 99.3 | 99 | 99.5 |
| | Branched olefin | 0.2 | 0.7 | 1 | 0.5 |
| Distribution of double bonds in linear olefin (% by mass) | Position 1 | 1.6 | 0.9 | 0.3 | 0.5 |
| | Position 2 | 41.7 | 25 | 13.3 | 30.1 |
| | Position 3 | 29.3 | 21.9 | 12.6 | 25.5 |
| | Position 4 | 15.7 | 19 | 13.9 | 18.8 |
| | Position 5 | 6.3 | 13.6 | 14.8 | 11.1 |
| | Position 6 | 3.9 | 8.6 | 13.7 | 7 |
| | Position 7 | 1.1 | 5.6 | 12.6 | 3.5 |
| | Position 8 | 0.2 | 2.7 | 9.4 | 3.5 |
| | Position 9 | 0.2 | 2.7 | 9.4 | 0 |
| Total content of olefins having double bonds at positions 6-9 in linear olefin (% by mass) | | 5.4 | 19.6 | 45.1 | 14.0 |

The distribution of double bonds in the internal olefins was determined by the aforementioned method.
In the olefins having 18 carbons, an internal olefin with a double bond at position 8 and an internal olefin with a double bond at position 9 cannot be structurally distinguished from each other but can be distinguished when they are sulfonated. Therefore, a value obtained by dividing the amount of the internal olefin with a double bond at position 8 by 2 is shown in the column of each of the position 8 and position 9, for convenience.

Further, in the olefin having 16 carbons, an internal olefin with a double bond at position 7 and an internal olefin with a double bond at position 8 cannot be structurally distinguished from each other but can be distinguished when they are sulfonated. Therefore, a value obtained by dividing the amount of the internal olefin with a double bond at position 7 by 2 is shown in the column of each of the position 7 and position 8, for convenience.

Production Examples 1 to 4

Production of Component (a-1) to Component (a-3) and Component (d-2)

Any one of internal olefins A1 to A3 and D obtained in Production Examples A1 to A3 and D was subjected to sulfonation reaction using a thin film-type sulfonation reactor equipped with an external jacket and sulfur trioxide gas, while passing cooling water at 20° C. through the external jacket. In the sulfonation reaction, the molar ratio, $SO_3$/internal olefin, was set to 1.09. The sulfonated product obtained was added to an alkali aqueous solution prepared using sodium hydroxide in a molar amount of 1.5 times the theoretical acid value, followed by neutralization at 30° C. for 1 hour under stirring. The neutralized product was heated in an autoclave at 160° C. for 1 hour for hydrolysis, to obtain a crude product of internal sodium olefin sulfonate. 300 g of the crude product was transferred to a separation funnel, and 300 mL of ethanol was added thereto. Thereafter, 300 mL of petroleum ether was added per time, to extract and remove oil-soluble impurities. At this time, inorganic compounds (mainly containing sodium sulfate) precipitated at the interface of oil and water due to the addition of ethanol were also separated and removed from the water phase by the oil-water separation operation. The extraction and removal operation was repeated 3 times. The water phase was evaporated to dryness, to obtain an internal sodium olefin sulfonate. Thus, (a-1) to (a-3) and (d-2) were obtained. Further, (a-1) and (a-2) or (a-2) and (a-3) were mixed, to obtain (a-4) and (a-5) described below.

The proportion of the content of the internal olefin sulfonate having a sulfonate group attached thereto was determined by high performance liquid chromatography/mass spectrometer (HPLC-MS). Specifically, identification was conducted by separating the hydroxy form having a sulfonate group attached thereto by high performance liquid chromatography (HPLC), and subjecting the hydroxy form to mass spectrometer (MS). As a result, each proportion was determined from the resulting HPLC-MS peak area. In the present description, each proportion determined from the peak area was calculated as proportion by mass.

The devices and the conditions used for the determination were as follows.
HPLC apparatus: "LC-20ASXR" (manufactured by SHIMADZU CORPORATION)
Column: "ODS Hypersil (R)" (4.6×250 mm, particle size: 3 μm, manufactured by Thermo Fisher SCIENTIFIC K.K.)
Sample preparation: Diluted 1000-fold with methanol
Eluent A: 10 mM ammonium acetate-added water
Eluent B: 10 mM ammonium acetate-added methacrylonitrile/water=95/5 (v/v) solution
Gradient: 0 minutes (A/B=60/40)→15.1 to 20 minutes (30/70)→20.1 to 30 minutes (60/40)
MS apparatus: "LCMS-2020" (manufactured by SHIMADZU CORPORATION)
ESI detection: Anion detection, m/z: 349.15 (component (A) having 18 carbons), 321.10 (component (D) having 16 carbons), column temperature (40° C.), flow rate (0.5 mL/min), injection volume (5 μL)

Table 2 shows the positional distribution of carbons to which sulfonate groups were bound in (a-1), (a-2), (a-3), (a-4), (a-5), and (d-2) obtained.

TABLE 2

|  |  |  | Components (A) | | | | | Component (D) |
|---|---|---|---|---|---|---|---|---|
|  |  |  | (a-1) | (a-2) | (a-3) | (a-4) | (a-5) | (d-2) |
| The number of carbons in hydrocarbon group | | | 18 | 18 | 18 | 18 | 18 | 16 |
| Distribution of sulfonate groups (% by mass) | Position 1 | | 1.6 | 1.4 | 0.6 | 1.6 | 0.8 | 1.5 |
| | (IO-1S) | Position 2 | 31.5 | 22.1 | 12.8 | 29.4 | 14.8 | 24.1 |
| | | Position 3 | 25.1 | 17.2 | 10.7 | 23.4 | 12.1 | 19.9 |
| | | Position 4 | 24.7 | 21.8 | 16.6 | 24.1 | 17.7 | 24.6 |
| | (IO-2S) | Position 5-Position 9 | 17.1 | 37.5 | 59.3 | 21.5 | 54.6 | 29.9 |
| (IO-1S)/(IO-2S) (mass ratio) | | | 4.8 | 1.6 | 0.68 | 3.6 | 0.82 | 2.3 |

<Blending Components>

In Examples and Comparative Examples, the following components were used.

[Component (A)]

(a-1): An internal sodium olefin sulfonate obtained from internal olefin A1

The mass ratio of the hydroxy form (sodium hydroxyalkanesulfonate)/the olefin form (sodium olefin sulfonate) in the internal sodium olefin sulfonate was 82/18.

(a-2): An internal sodium olefin sulfonate obtained from internal olefin A2

The mass ratio of the hydroxy form (sodium hydroxyalkanesulfonate)/the olefin form (sodium olefin sulfonate) in the internal sodium olefin sulfonate was 83/17.

(a-3): An internal sodium olefin sulfonate obtained from internal olefin A3

The mass ratio of the hydroxy form (sodium hydroxyalkanesulfonate)/the olefin form (sodium olefin sulfonate) in the internal sodium olefin sulfonate was 83/17.

(a-4): An internal sodium olefin sulfonate obtained by mixing (a-1) and (a-2) above The mass ratio of the hydroxy form (sodium hydroxyalkanesulfonate)/the olefin form (sodium olefin sulfonate) in the internal sodium olefin sulfonate was 83/17.

(a-5): An internal sodium olefin sulfonate obtained by mixing (a-2) and (a-3) above The mass ratio of the hydroxy form (sodium hydroxyalkanesulfonate)/the olefin form (sodium olefin sulfonate) in the internal sodium olefin sulfonate was 83/17.

The mass ratio of the olefin form/the hydroxy form in the internal sodium olefin sulfonate was determined by high performance liquid chromatography/mass spectrometer (HPLC-MS). Specifically, identification was conducted by separating the hydroxy form and the olefin form from each other by high performance liquid chromatography (HPLC) and subjecting each form to a mass spectrometer (MS). As a result, the proportion of each form was determined from the HPLC-MS peak area.

The devices and the conditions used for the determination were as follows.
HPLC apparatus: "Agilent 1100" (manufactured by Agilent Technologies, Inc.)
Column: "L-columnODS" (4.6×150 mm, manufactured by Chemicals Evaluation and Research Institute, Japan) Sample preparation: Diluted 1000-fold with methanol
Eluent A: 10 mM ammonium acetate-added water
Eluent B: 10 mM ammonium acetate-added methanol
Gradient: 0 minutes (A/B=30/70%)→10 minutes (30/70%)→55 minutes (0/100%)→65 minutes (0/100%)→66 minutes (30/70%)→75 minutes (30/70%)
MS apparatus: "Agilent 1100 MSSL (G1946D)" (manufactured by Agilent Technologies, Inc.)
MS detection: Anion detection, m/z: 60 to 1600, UV: 240 nm
[Component (B)]
(b-1): Calcium chloride (special grade, manufactured by Wako Pure Chemical Industries, Ltd.)
[Component (C)]
(C1-2-1): Zeolite (Zeolite A, manufactured by Zeobuilder Co.)
(C1-3-1): Sodium tripolyphosphate (Thai polyphosphate & Chemicals Co., Ltd.)
[Optional Components]
[Component (D): Surfactants Other than Component (A)]
(d-1): α-sodium olefin sulfonate having 20 carbons
(d-2): An internal sodium olefin sulfonate obtained from internal olefin D The mass ratio of the olefin form (sodium olefin sulfonate)/the hydroxy form (sodium hydroxyalkanesulfonate) in the internal sodium olefin sulfonate was 16/84 (determined by the aforementioned method).
(d-3): Sodium alkylbenzene sulfonate (alkyl composition: 010/C11/C12/C13=11/29/34/26 (mass ratio), the mass average number of carbons=17.75)
(d-4): Polyoxyethylene lauryl ether (compound with an average number of added moles of oxyethylene group: 10 mol, HLB=14.0, $R^1$: a lauryl group, m:0, $A^1O$: an ethyleneoxy group, n:10, and $R^2$: a hydrogen atom in formula (d5))
(d-5): Polyoxyalkylene lauryl ether (compound to which an average of 9 mol of an ethyleneoxy group was added, an average of 2 mol of a propyleneoxy group was added, and then an average of 9 mol of an ethyleneoxy group was added, per mol of lauryl alcohol, HLB=14.5, $R^1$: a lauryl group, m:0, $A^1O$: an ethyleneoxy group and a propyleneoxy group, n:20, and $R^2$: a hydrogen atom in formula (d5))
(d-6): Polyoxyethylene lauryl ether (compound with an average number of added moles of oxyethylene group: 3 mol, HLB=8.3, $R^1$: a lauryl group, m:0, $A^1O$: an ethyleneoxy group, n:3, and $R^2$: a hydrogen atom in formula (d5))
(d-7): A softening base obtained in Production Example 5 below Production Example 5

Production of Softening Base (d-7)

A softening base containing a cationic surfactant was obtained by the following method.

195 g (0.71 mol) of mixed fatty acid 1 (mass ratio of palmitic acid/stearic acid/oleic acid/linoleic acid: 30/30/35/5, the average molecular weight: 275) was mixed with 54.4 g (0.37 mol) of triethanolamine, followed by reaction at 180 to 185° C. (under normal pressure) for 3 hours, and thereafter the pressure was reduced to 200 mmHg, followed by further aging for 3 hours. Thereafter, the pressure was returned to normal with nitrogen, followed by cooling to 100° C., to obtain 392 g of a dehydrated condensate. The acid value (according to JIS K0070) of the condensate obtained was 0.7 mgKOH/g, and the total amine value (according to JIS K2501) thereof was 196 mgKOH/g. Subsequently, the temperature of 392 g of the dehydrated condensate was adjusted to 70 to 75° C., and dimethyl sulfate equivalent to 0.98 equivalent relative to the amine equivalent of the dehydrated condensate based on the amine value of the dehydrated condensate was added dropwise thereto over 2.5 hours. After the addition was completed, the mixture was further kept at 50 to 55° C. for 3 hours, to obtain a reaction product. In order to reduce the viscosity of the reaction product for facilitating the handling, 100 g of ethanol was added and mixed. A solid quaternary ammonium salt in the reaction product obtained was used as component (d-7).
[Water]
Ion-Exchanged Water
<Method for Evaluating Softness>
(1) Pretreatment of Textile Product for Evaluation Generally, treatment agents such as spinning oils used in spinning cotton threads used for cotton towels or knitted cotton cloths and lubricants used in producing cotton towels are present in commercially available cotton towels or knitted cotton cloths. In this evaluation, the textile products for evaluation were pretreated by the method shown below for eliminating the influence of such treatment agents. The pretreatment in this evaluation includes a treatment operation for reducing the amount of the treatment agents present in commercially available cotton towels or knitted cotton cloths by the washing operation shown below.
(1-1) Pretreatment of Cotton Towels 24 pieces of cotton towels (TW-220, cotton 100%, manufactured by Takei towel Co., Ltd.) were subjected to the following washing operation, followed by drying in an environment of 23° C. and 45RH for 24 hours.

The washing operation was composed of washing operation (1) and washing operation (2).

As washing operation (1), washing was performed twice continuously, using a surfactant in the standard course of a fully automatic washing machine (NA-F702P, manufactured by Panasonic Corporation). In washing operation (1), 4.7 g of EMULGEN 108 (nonionic surfactant, manufactured by Kao Corporation) was used as the surfactant during washing in the standard course. Further, the conditions of the standard course employed in washing operation (1) included a water volume of 47 L, a water temperature of 20° C., washing for 9 minutes, soak rinse twice, and dehydration for 3 minutes.

Further, as washing operation (2), washing operation under the same conditions as in washing operation (1)

described above but using no surfactants during washing in the standard course was repeated 3 times after washing operation (1).

In this pretreatment, a series of washing operations composed of washing operation (1) and washing operation (2) under the aforementioned conditions were performed.

(1-2) Pretreatment of Knitted Cotton Cloths 1.7 kg of knitted cotton cloths (Cotton knit non-sill (non-mercerized), cotton 100%, manufactured by SHIKI-SENSHA CO., LTD.) were subjected to the same washing operation as in pretreatment of cotton towels (1-1) mentioned above, followed by drying in an environment of 23° C. and 45% RH for 24 hours.

(1-3) Pretreatment of Polyester Cloths 1.6 kg of polyester cloths were subjected to the following washing operation 5 times continuously, followed by drying under conditions of 20° C. and 43° RH for 24 hours.

The polyester cloths were prepared by cutting a commercially available polyester jersey (polyester 100%, manufactured by Senshoku Shizai K.K., Tanigashira Shoten) into 30 cm×30 cm.

As the washing operation, washing was performed using a surfactant in the standard course of a fully automatic washing machine (Hitachi automatic washing machine, NW-6CY). In this washing operation, 4.5 g of a lauryl alcohol ethylene oxide adduct (nonionic surfactant, the average number of added moles: 8) was used as a surfactant during washing in the standard course. Further, the conditions of the standard course employed in the washing operation were a water volume of 45 L, a water temperature of 20° C., washing for 10 minutes, and soak rinse twice. In this pretreatment, the washing operation under such conditions was performed 5 times continuously.

(2) Softening Treatment of Textile Products for Evaluation 6.0 L of tap water (at 20° C. and 3.5° dH, as calculated by the aforementioned method for determining the hardness of water) was poured into an electric bucket type washing machine (model number "N-BK2"), manufactured by Panasonic Corporation, and 12 g of the softening agent compositions for textile products according to Examples or Comparative Examples shown in the table was put therein as a finishing agent composition for textile products, followed by stirring for 1 minute. Thereafter, 2 pieces of cotton towels (140 g), 4 pieces of knitted cotton cloths (140 g), or 170 g of polyester cloths, which had been pretreated by the aforementioned methods, were put therein, followed by softening for 3 minutes. After the softening, dehydration was performed for 1 minute using a HITACHI two-tub washing machine (model number "PS-H35L"). Subsequently, 6.0 L of the tap water was poured into the aforementioned bucket washing machine, and the cotton towels, the knitted cotton cloths, or the polyester cloths after the dehydration using the HITACHI two-tub washing machine were further put therein, followed by rinsing for 3 minutes. Thereafter, the same dehydration was performed for 1 minute using the two-tub washing machine. Such softening was performed 3 times in total, followed by standing under conditions of 20° C. and 43% RH for 12 hours for drying.

(3) Evaluation of Softness

The cotton towels, the knitted cotton cloths, or the polyester cloths that were washed, rinsed, and dried with the softening agent compositions for textile products having the compositions described in Table 2 were scored for softness by 6 skilled persons in evaluating the texture of textile products based on the following criteria, and the average was calculated. Table 2 shows two-digit values of rounded significant figures.

−1 . . . Finished with less softness than the cotton towels, knitted cotton cloths, or polyester cloths treated with the composition of Comparative Example 1

0 . . . Finished with softness equivalent to the cotton towels, knitted cotton cloths, or polyester cloths treated with the composition of Comparative Example 1

1 . . . Finished with slightly more softness than the cotton towels, knitted cotton cloths, or polyester cloths treated with the composition of Comparative Example 1

2 . . . Finished with more softness than the cotton towels, knitted cotton cloths, or polyester cloths treated with the composition of Comparative Example 1

3 . . . Finished with much more softness than the cotton towels, knitted cotton cloths, or polyester cloths treated with the composition of Comparative Example 1

<Method for Evaluating Water Absorbency>

2 pieces were selected at random from the cotton towels or the knitted cotton cloths that were evaluated for softness in (3) Method for evaluating softness, and a cloth piece with a length of 25 cm and a width of 2.5 cm was cut out from each of the selected 2 pieces. The point at 2 cm from the end of the short side along the long-side direction was marked with a black aqueous marker. Taking the marked point as 0 cm, a mark was made every 1 cm along the long side of direction up to the maximum of 20 cm. The aforementioned cloth piece was disposed with the long-side direction being perpendicular to the water surface, the end marked as 0 cm facing downward, and the opposite short side facing upward. Thereafter, 2 L of tap water at 25° C. was put into a beaker made of plastic (volume: 2 liters), and the short side (lower end) of the cloth piece was immersed in the water so that the water surface reached the 0-cm mark. Taking the time when the water surface reached 0 cm as 0 minutes, the water height after 15 minutes was determined. The tip where the black mark bled and the black ink developed by chromatography was taken as the water height. The table shows an average of the 2 cloth pieces. A greater water absorbency height indicates a better water absorbency.

Example 1 and Comparative Example 1

Preparation of Softening Agent Composition for Textile Products of Example 1

A Teflon (R) stir bar with a length of 5 cm was put into a 200 mL glass beaker, and the mass was determined. Then, 80 g of ion-exchanged water at 20° C. and 5 g of component (a-1) as an active component was put therein as component (A), and the upper surface of the beaker was sealed with a food wrapping film (Saran Wrap (R), manufactured by Asahi Kasei Home Products Corporation). The beaker with contents was put into a water bath at 60° C. provided within a magnetic stirrer, followed by stirring at 100 r/min for 30 minutes with the temperature of the water inside the water bath falling within a range of 60±2° C. Thereafter, the water inside the water bath was replaced with tap water at 5° C. and then cooled until the temperature of the composition inside the beaker reached 20° C. Subsequently, the film was removed, and ion-exchanged water was put therein so that the mass of the contents was 100 g, followed by stirring again at 100 r/min for 30 seconds, to obtain a softening agent composition for textile products of Example 1 in Table 3.

Preparation of Softening Agent Composition for Textile Product of Comparative Example 1

A softening agent composition for textile products of Comparative Example 1 was prepared by the same method as in "Preparation of softening agent composition for textile product of Example 1" described above, except that component (d-3) was put therein instead of component (a-1).

Using the softening agent compositions for textile products obtained, cotton towels were evaluated for softness by the aforementioned method. Table 3 shows the results. Cotton towels washed with the softening agent composition for textile products of Example 1 were finished with more softness than cotton towels washed with the softening agent composition for textile products of Comparative Example 1.

Examples 2 to 10 and Comparative Examples 2 and 3

Examples 2 to 10 were prepared in the same manner as in the preparation of the softening agent composition for textile products of Example 1 with the compositions in Table 3. The % by mass was adjusted using ion-exchanged water. In the case of using component (C), component (C) was put into the beaker after component (A) was put therein.

Comparative Examples 2 and 3 were prepared in the same manner as in the preparation of the softening agent composition for textile products of Comparative Example 1 with the compositions in Table 3. The % by mass was adjusted using ion-exchanged water.

Using the softening agent compositions for textile products obtained, cotton towels were evaluated for softness by the aforementioned method. Table 3 shows the results.

The softening agent composition for textile products containing a zeolite was sufficiently stirred before weighing, so as to be weighed with the zeolite uniformly dispersed.

TABLE 3

| | | | | Examples | | | | | | | | | | Comparative Examples | | |
|---|---|---|---|---|---|---|---|---|---|---|---|---|---|---|---|---|
| | | | | 1 | 2 | 3 | 4 | 5 | 6 | 7 | 8 | 9 | 10 | 1 | 2 | 3 |
| Softening agent composition for textile products | Amounts blended (% by mass) | (A) | (a-1) | 10 | | | | | | | | | | | | |
| | | | (a-2) | | 10 | | | | 8 | 6 | 10 | 10 | 10 | | | |
| | | | (a-3) | | | 10 | | | | | | | | | | |
| | | | (a-4) | | | | 10 | | | | | | | | | |
| | | | (a-5) | | | | | 10 | | | | | | | | |
| | | (C) | (c1-2-1) | | | | | | | | 5 | 25 | | | | |
| | | | (c1-3-1) | | | | | | | | | | 25 | | | |
| | | (D) | (d-1) | | | | | | | | | | | 10 | | |
| | | | (d-2) | | | | | | | | | | | | 10 | |
| | | | (d-3) | | | | | | | | | | | | | 10 |
| | Ion-exchanged water | | | Balance | Balance | Balance | Balance | Balance | Balance | Balance | Balance | Balance | Balance | Balance | Balance | Balance |
| | Total | | | 100 | 100 | 100 | 100 | 100 | 100 | 100 | 100 | 100 | 100 | 100 | 100 | 100 |
| Softness (cotton towel) | | | | 2.5 | 2.2 | 2.0 | 2.3 | 2.2 | 1.5 | 0.67 | 2.0 | 0.50 | 0.50 | Reference | −0.67 | 0 |
| Water absorbency (cotton towel, water absorption height: cm) | | | | 8.5 | 8.7 | 9.0 | 8.6 | 8.9 | 8.9 | 9.0 | 9.0 | 9.5 | 9.5 | 9.5 | 9.0 | 9.0 |

Examples 11 to 16 and Comparative Examples 4 and 5

Examples 11 to 16 were prepared in the same manner as in the preparation of the softening agent composition for textile products of Example 1 with the compositions in Table 4. The % by mass was adjusted using ion-exchanged water. In the case of using component (D), component (D) was put into the beaker after component (A) was put therein.

Comparative Example 4 was prepared in the same manner as in the preparation of the softening agent composition for textile products of Comparative Example 1 with the composition in Table 4. The % by mass was adjusted using ion-exchanged water.

In Comparative Example 5, a softening agent composition for textile products containing component (D) was prepared, the amount of component (D) being shown in Table 4. The % by mass was adjusted using ion-exchanged water.

Using the softening agent compositions for textile products obtained, knitted cotton cloths were evaluated for softness by the aforementioned method. Table 4 shows the results. Comparative Example 4 was used as a reference for evaluating the softness.

In Table 4, the knitted cotton cloths gave a fresher feeling in Examples 11, 12, 14, 15, and 16 than in Example 13 when they were treated by the aforementioned method with the softening agent compositions for textile products of Examples 11 to 16.

TABLE 4

| | | | | Examples | | | | | | Comparative Examples | |
|---|---|---|---|---|---|---|---|---|---|---|---|
| | | | | 11 | 12 | 13 | 14 | 15 | 16 | 4 | 5 |
| Softening agent composition for textile products | Amounts blended (% by mass) | (A) | (a-1) | | | | | | | | |
| | | | (a-2) | 5 | 7 | 10 | 9 | 8 | 5 | | |
| | | | (a-3) | | | | | | | | |
| | | (D) | (d-3) | | | | | | | 5 | |
| | | | (d-4) | 5 | 3 | | | | | 5 | |
| | | | (d-5) | | | | 1 | 2 | | | |
| | | | (d-6) | | | | | | 5 | | |
| | | | (d-7) | | | | | | | | 10 |
| | | Ion-exchanged water | | Balance | Balance | Balance | Balance | Balance | Balance | Balance | Balance |
| | | Total | | 100 | 100 | 100 | 100 | 100 | 100 | 100 | 100 |
| | | (D)/(A) (mass ratio) | | 1.00 | 0.43 | 0 | 0.11 | 0.25 | — | — | — |
| Softness (knitted cotton cloth) | | | | 1.2 | 2.0 | 3.0 | 2.2 | 2.0 | 0.17 | Reference | 3.0 |
| Water absorbency (knitted cotton cloth, water absorption height: cm) | | | | 9.0 | 8.8 | 8.7 | 8.8 | 9.0 | 9.3 | 9.5 | 5.9 |

Examples 17 to 22

Examples 17 to 22 were prepared in the same manner as in the preparation of the softening agent composition for textile products of Example 1 with the compositions in Table 5. The % by mass was adjusted using ion-exchanged water. In the case of using component (D) or component (B) and component (D), component (D) or component (B) and component (D) were put into the beaker after component (A) was put therein.

Using the softening agent compositions for textile products obtained, knitted cotton cloths were evaluated for softness by the aforementioned method. However, water adjusted to 2° dH by adding hardness components to ion-exchanged water was used for softening the textile products, instead of tap water [at 20° C. with Ca/Mg=8/2 (mass ratio), as calculated by the aforementioned method for determining the hardness of water]. Table 4 shows the results. Example 17 was used as a reference for the evaluation. Example 17 had the same composition as Example 12 in Table 4 and exhibited a softness higher than Comparative Example 4 by 2 points, as shown in Table 4.

TABLE 5

| | | | | Examples | | | | | |
|---|---|---|---|---|---|---|---|---|---|
| | | | | 17 | 18 | 19 | 20 | 21 | 22 |
| Softening agent composition for textile products | Amounts blended (% by mass) | (A) | (a-2) | 7 | 7 | 7 | 7 | 7 | 7 |
| | | (B) | (b-1) | | 1.5 | 8 | 0.01 | 0.1 | 0.5 |
| | | (D) | (d-4) | 3 | 3 | 3 | 3 | 3 | 3 |
| | | Ion-exchanged water | | Balance | Balance | Balance | Balance | Balance | Balance |
| | | Total | | 100 | 100 | 100 | 100 | 100 | 100 |
| | | (D)/(A) (mass ratio) | | 0.43 | 0.43 | 0.43 | 0.43 | 0.43 | 0.43 |
| Softness (knitted cotton cloth) | | | | Reference | 1.7 | 3.0 | 1.2 | 1.3 | 1.5 |
| Water absorbency (knitted cotton cloth, water absorption height: cm) | | | | 8.8 | 8.8 | 8.5 | 8.8 | 8.8 | 8.8 |

Example 23 and Comparative Example 6

Example 23 was prepared in the same manner as in the preparation of the softening agent composition for textile products of Example 1 with the composition in Table 6. The % by mass was adjusted using ion-exchanged water.

Comparative Example 6 was prepared in the same manner as in the preparation of the softening agent composition for textile products of Comparative Example 1 with the composition in Table 6. The % by mass was adjusted using ion-exchanged water.

Using the softening agent compositions for textile products obtained, knitted cotton cloths and polyester cloths were evaluated for softness by the aforementioned method. Table 6 shows the results. The results for the same textile products of Comparative Example 6 were used as references for the evaluation.

TABLE 6

|  |  |  |  | Example 23 | Comparative Example 6 |
|---|---|---|---|---|---|
| Softening agent composition for textile products | Amounts blended (% by mass) | (A) | (a-2) | 10 | |
| | | (D) | (d-3) | | 10 |
| | | Ion-exchanged water | | Balance | Balance |
| | | Total | | 100 | 100 |
| | Softness | Knitted cotton cloth | | 2.2 | Reference |
| | | Polyester cloth | | 1.0 | Reference |

In Table 6, when the textile products for evaluation were knitted cotton cloths, the difference between Example 23 and Comparative Example 6 in softness evaluation point was 2.2.

Meanwhile, when the textile products for evaluation were polyester cloths, the difference between Example 23 and Comparative Example 6 in softness evaluation point was 1.0.

It is understood from these results that the finishing agent composition for textile products, particularly, the softening agent composition for textile products according to the present invention exerts a more excellent effect of imparting softness to textile products containing cotton fibers.

Example 24 and Comparative Example 7

(1) Treatment of Textile Products for Evaluation

Using the softening agent compositions for textile products in Table 7, treatment method A or treatment method B described below was performed. Example 24 has the same composition as Example 2 in Table 3, and Comparative Example 7 has the same composition as Comparative Example 5 in Table 4.

(1-1) Treatment Method A
Step 1A 6.0 L of tap water (at 20° C. with 3.5° dH, as calculated by the aforementioned method for determining the hardness of water) was poured into an electric bucket type washing machine (model number "N-BK2"), manufactured by Panasonic Corporation. Subsequently, a lauryl alcohol ethylene oxide adduct (nonionic surfactant, the average number of added moles: 8) as a surfactant was put therein so that the concentration in water was 200 mg/kg, followed by stirring for 10 minutes. Thereafter, 2 pieces (140 g) of cotton towels, which had been pretreated by the aforementioned method, were put therein, followed by stirring for 10 minutes. Then, using a HITACHI two-tub washing machine (model number "PS-H35L"), the aforementioned 2 pieces of cotton towels were dehydrated for 1 minute. Thereafter, 6.0 L of tap water as described above was poured into the aforementioned bucket washing machine, and the aforementioned 2 pieces of dehydrated cotton towels were put therein, followed by rinsing for 3 minutes. Thereafter, using a HITACHI two-tub washing machine (model number "PS-H35L"), the aforementioned 2 pieces of cotton towels were dehydrated for 1 minute. Thereafter, using a HITACHI two-tub washing machine (model number "PS-H35L"), the aforementioned 2 pieces of cotton towels were dehydrated for 1 minute.

Step 2A 6.0 L of tap water as described above was poured into the aforementioned bucket washing machine, and 12 g of the softening agent composition for textile products described in Table 7 was put therein, followed by stirring for 1 minute. Thereafter, the 2 pieces of dehydrated cotton towels obtained in step 1A above were put therein, followed by finishing for 3 minutes. Subsequently, using a HITACHI two-tub washing machine (model number "PS-H35L"), the aforementioned 2 pieces of cotton towels were dehydrated for 1 minute, followed by standing under conditions of 20° C. and 43% RH for 12 hours for drying.

(1-2) Treatment Method B

The same operation was performed except that 200 mg/kg of sodium alkylbenzene sulfonate (NEOPELEX G-25, active components 25%) in terms of the concentration of active components was used instead of the nonionic surfactant used in step 1A in (1-1) Treatment method A described above.

(2) Evaluation of Softness

The softness was evaluated in the same manner as in the evaluation of softness in Example 1, etc., except that cotton towels treated by treatment method A were used as a reference.

That is, using cotton towels subjected to treatment method A with the softening agent composition for textile products of Example 24 as a reference, cotton towels subjected to treatment method B using the softening agent composition for textile products of Example 24 were evaluated for softness in Example 24.

Likewise, using cotton towels subjected to treatment method A with the softening agent composition for textile products of Comparative Example 7 as a reference, cotton towels subjected to treatment method B with the softening agent composition for textile products of Comparative Example 7 were evaluated for softness in Comparative Example 7.

Table 7 shows the results.

TABLE 7

|  |  |  |  | Example 24 | Comparative Example 7 |
|---|---|---|---|---|---|
| Softening agent composition for textile products | Amounts blended (% by mass) | (A) | (a-2) | 10 | |
| | | (D) | (d-7) | | 10 |
| | | Ion-exchanged water | | Balance | Balance |
| | | Total | | 100 | 100 |

TABLE 7-continued

|  |  | Example 24 | Comparative Example 7 |
|---|---|---|---|
| Softness | Treatment method for textile products A | Reference | Reference |
|  | Treatment method for textile products B | 0 | −1 |

In this example, a method for treating textile products including: step 1 of washing the textile products with a washing liquid containing one or more surfactants selected from anionic surfactants and nonionic surfactants; and step 2 of contacting the textile products after step 1 with a treatment liquid for textile products obtained from the composition of Example 24 or Comparative Example 7 was performed.

In the softening agent composition for textile products of Example 24, the softness of cotton towels treated by treatment method A using a nonionic surfactant in step 1 and the softness of cotton towels treated by treatment method B using an anionic surfactant in step 1 were equivalent to each other.

Meanwhile, in the softening agent composition for textile products of Comparative Example 7, the softness of cotton towels treated by treatment method B using an anionic surfactant in step 1 was reduced as compared with the softness of cotton towels treated by treatment method A using a nonionic surfactant in step 1, and thus finishing with equivalent softness was not achieved.

The invention claimed is:

1. A finishing agent composition for textile products, comprising a fiber modifier consisting of an internal olefin sulfonate having 17 or more and 24 or less carbons, and a polyvalent metal salt.

2. The finishing agent composition for textile products according to claim 1, wherein
a content of 1-olefin sulfonate in the internal olefin sulfonate having 17 or more and 24 or less carbons is 10% by mass or less.

3. The finishing agent composition for textile products according to claim 1, wherein the polyvalent metal salt is one or more polyvalent metal salts selected from inorganic polyvalent metal salts and organic polyvalent metal salts.

4. The finishing agent composition for textile products according to claim 3, wherein the inorganic polyvalent metal salts are one or more inorganic polyvalent metal salts selected from inorganic divalent metal salts and inorganic trivalent metal salts, and the organic polyvalent metal salts are one or more organic polyvalent metal salts selected from organic divalent metal salts and organic trivalent metal salts.

5. The finishing agent composition for textile products according to claim 4, wherein the inorganic divalent metal salts are one or more inorganic divalent metal salts selected from calcium salts and magnesium salts, and the inorganic trivalent metal salts are aluminum salts.

6. The finishing agent composition for textile products according to claim 4, wherein the organic polyvalent metal salts are organic polyvalent metal salts having 1 or more and 8 or less carbons.

7. The finishing agent composition for textile products according to claim 1, wherein a content of the polyvalent metal salts in the finishing agent composition for textile products is 10 mg/kg or more and 20% by mass or less.

8. The finishing agent composition for textile products according to claim 1, wherein
a content of a metal ion chelating agent in the finishing agent composition for textile products is 0% by mass or more and 20% by mass or less.

9. The finishing agent composition for textile products according to claim 8, wherein the metal ion chelating agent is one or more selected from (C1) metal ion chelates that are inorganic compounds and (C2) metal ion chelating agents that are organic compounds.

10. The finishing agent composition for textile products according to claim 9, wherein (C1) is one or more metal ion chelates selected from (C1-1) alkali metal silicates, (C1-2) aluminosilicates, and (C1-3) tripolyphosphates.

11. The finishing agent composition for textile products according to claim 9, wherein (C2) is one or more metal ion chelating agents selected from (C2-1) di- or higher and tetra- or lower valent carboxylic acids or salts thereof free from amino groups and having 4 or more and 12 or less carbons, (C2-2) di- or higher and tetra- or lower valent carboxylic acids or salts thereof containing an amino group and having 4 or more and 10 or less carbons, and (C2-3) compounds having a phosphonate group or a salt thereof in the molecule.

12. A method for finishing textile products, comprising:
contacting the textile products with a treatment liquid for textile products containing water, an internal olefin sulfonate having 17 or more and 24 or less carbons in an amount of 0.002% by mass or more and 6% by mass or less relative to the textile products and a polyvalent metal salt.

13. The method for finishing textile products according to claim 12, wherein
a content of 1-olefin sulfonate in the internal olefin sulfonate having 17 or more and 24 or less carbons is 10% by mass or less.

14. The method for finishing textile products according to claim 12, wherein
the internal olefin sulfonate having 17 or more and 24 or less carbons comprises an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

15. The method for finishing textile products according to claim 12, wherein the internal olefin sulfonate having 17 or more and 24 or less carbons contains an internal olefin sulfonic acid having 18 or more carbons in an amount of 80% by mass or more, and an internal olefin sulfonate having 20 or more and 24 or less carbons in an amount of 20% by mass or less.

16. The method for finishing textile products according to claim 12, wherein a content of 1-olefin sulfonate in the internal olefin sulfonate having 17 or more and 24 or less carbons is 10% by mass or less.

17. A method for finishing textile products, comprising:
contacting the textile products with a treatment liquid for textile products containing water, an internal olefin sulfonate having 17 or more and 24 or less carbons in an amount of 0.002% by mass or more and 6% by mass or less relative to the textile products and a polyvalent metal salt;
wherein the treatment liquid is obtained by mixing the finishing agent composition for textile products according to claim 1 with water.

18. A method for treating textile products, comprising:
step 1 of washing the textile products with a washing liquid containing one or more surfactants selected from anionic surfactants and nonionic surfactants; and
step 2 of contacting the textile products after step 1 with a treatment liquid for textile products containing water, an internal olefin sulfonate having 17 or more and 24 or less carbons in an amount of 0.002% by mass or more and 6% by mass or less relative to the textile products and a polyvalent metal salt.

19. The method for treating textile products according to claim 18, wherein
the internal olefin sulfonate having 17 or more and 24 or less carbons comprises an internal olefin sulfonate having 17 or more and 24 or less carbons with the sulfonate group at position 2 or higher and 4 or lower (IO-1S) and an internal olefin sulfonate having 17 or more and 24 or less carbons with the sulfonate group at position 5 or higher (IO-2S), wherein a mass ratio (IO-1S)/(IO-2S) of (IO-1S) to (IO-2S) is 0.6 or more and 6 or less.

20. The method for treating textile products according to claim 18, wherein the internal olefin sulfonate having 17 or more and 24 or less carbons has 18 or more and 20 or less carbons.

* * * * *